(12) United States Patent
Yamamoto

(10) Patent No.: US 12,295,780 B2
(45) Date of Patent: May 13, 2025

(54) ULTRASOUND DIAGNOSTIC APPARATUS, CONTROL METHOD OF ULTRASOUND DIAGNOSTIC APPARATUS, AND PROCESSOR FOR ULTRASOUND DIAGNOSTIC APPARATUS

(71) Applicant: FUJIFILM Corporation, Tokyo (JP)

(72) Inventor: Katsuya Yamamoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 337 days.

(21) Appl. No.: 17/818,602

(22) Filed: Aug. 9, 2022

(65) Prior Publication Data

US 2022/0378394 A1 Dec. 1, 2022

Related U.S. Application Data

(63) Continuation of application No. PCT/JP2021/000019, filed on Jan. 4, 2021.

(30) Foreign Application Priority Data

Feb. 14, 2020 (JP) ................. 2020-023391

(51) Int. Cl.
  *A61B 8/06* (2006.01)
  *A61B 8/00* (2006.01)
  *A61B 8/08* (2006.01)
(52) U.S. Cl.
  CPC ............... *A61B 8/06* (2013.01); *A61B 8/463* (2013.01); *A61B 8/488* (2013.01); *A61B 8/5223* (2013.01); *A61B 8/5246* (2013.01)
(58) Field of Classification Search
  CPC .......... A61B 8/06; A61B 8/463; A61B 8/488; A61B 8/5223; A61B 8/5246
  See application file for complete search history.

(56) References Cited

U.S. PATENT DOCUMENTS

2012/0165686 A1\* 6/2012 Masuda ................. G16H 50/30
  600/481
2014/0303499 A1 10/2014 Toma et al.
(Continued)

FOREIGN PATENT DOCUMENTS

JP 5384919 B2 1/2014
JP 2014-188017 A 10/2014
(Continued)

OTHER PUBLICATIONS

International Search Report issued in PCT/JP2021/000019; mailed Feb. 16, 2021.
(Continued)

*Primary Examiner* — Sean A Frith
(74) *Attorney, Agent, or Firm* — Studebaker Brackett PLLC

(57) ABSTRACT

An ultrasound diagnostic apparatus (1) includes a first vascular wall detection unit (10) that detects a vascular wall in a minor axis direction by analyzing a B-mode image including a minor axis image of a blood vessel, a first blood vessel diameter calculation unit (11) that calculates a first blood vessel diameter from the vascular wall in the minor axis direction, a second vascular wall detection unit (12) that detects a vascular wall in a major axis direction by analyzing the B-mode image including a major axis image of the blood vessel, a second blood vessel diameter calculation unit (13) that calculates a second blood vessel diameter from the vascular wall in the major axis direction, a blood flow velocity calculation unit (15) that calculates a blood flow velocity based on Doppler data in a Doppler gate set on the B-mode image, and a blood flow rate measurement unit (16) that measures a blood flow rate based on the vascular wall in the major axis direction or the minor axis direction and the blood flow velocity, in which in a case where the second blood vessel diameter is within a determined range with (Continued)

respect to the first blood vessel diameter, the blood flow rate is automatically measured.

20 Claims, 13 Drawing Sheets

(56) References Cited

U.S. PATENT DOCUMENTS

| | | | |
|---|---|---|---|
| 2017/0086789 A1* | 3/2017 | Brandl | G16H 50/30 |
| 2017/0143309 A1* | 5/2017 | Seki | G16H 50/30 |
| 2019/0175035 A1* | 6/2019 | Van Der Horst | A61B 8/145 |
| 2020/0397409 A1 | 12/2020 | Inoue et al. | |

FOREIGN PATENT DOCUMENTS

| | | |
|---|---|---|
| JP | 2014-217745 A | 11/2014 |
| WO | 2013/124946 A1 | 8/2013 |
| WO | 2019/187649 A1 | 10/2019 |

OTHER PUBLICATIONS

International Preliminary Report on Patentability and Written Opinion issued in PCT/JP2021/000019; issued Aug. 11, 2022.

The extended European search report issued by the European Patent Office on Jun. 26, 2023, which corresponds to European Patent Application 21754288.5-1126 and is related to U.S. Appl. No. 17/818,602.

Extended European Search Report issued in EP 24 20 1190.6-1122 by the European Patent Office on Nov. 12, 2024, which is related to U.S. Appl. No. 17/818,602.

\* cited by examiner

ULTRASOUND DIAGNOSTIC APPARATUS, CONTROL METHOD OF ULTRASOUND DIAGNOSTIC APPARATUS, AND PROCESSOR FOR ULTRASOUND DIAGNOSTIC APPARATUS

CROSS-REFERENCE TO RELATED APPLICATIONS

This application is a Continuation of PCT International Application No. PCT/JP2021/000019 filed on Jan. 4, 2021, which claims priority under 35 U.S.C. § 119(a) to Japanese Patent Application No. 2020-023391 filed on Feb. 14, 2020. The above application is hereby expressly incorporated by reference, in its entirety, into the present application.

BACKGROUND OF THE INVENTION

1. Field of the Invention

The present invention relates to an ultrasound diagnostic apparatus that acquires B-mode data and Doppler data, a control method of the ultrasound diagnostic apparatus, and a processor for the ultrasound diagnostic apparatus.

2. Description of the Related Art

In the related art, an ultrasound diagnostic apparatus has been known as an apparatus for obtaining an image of the inside of a subject. The ultrasound diagnostic apparatus generally comprises an ultrasound probe comprising a transducer array in which a plurality of elements are arranged. In a state where the ultrasound probe is in contact with a body surface of the subject, an ultrasound beam is transmitted toward the inside of the subject from the transducer array and an ultrasound echo from the subject is received by the transducer array so that element data is acquired. Furthermore, the ultrasound diagnostic apparatus electrically processes the obtained element data to generate an ultrasound image of the corresponding site of the subject.

For example, WO2019/187649A discloses an ultrasound diagnostic apparatus that, in a state where an ultrasound image including a major axis image of a blood vessel of a subject is displayed on a display device, measures a blood flow rate in a designated blood vessel region based on a trigger that the blood vessel region on the ultrasound image displayed on the display device is designated by a user.

SUMMARY OF THE INVENTION

Here, in order to accurately measure the blood flow rate, it is desirable that the major axis image of the blood vessel included in the ultrasound image corresponds to a longitudinal cross section of the blood vessel such that the longitudinal cross section of the blood vessel passing through a center of the blood vessel, that is, a measured blood vessel diameter, is the maximum. However, in WO2019/187649A, the ultrasound image including the major axis image of the blood vessel is acquired after a position of the ultrasound probe is decided by determination based on an experience or the like of the user. Thus, an appropriate ultrasound image including the major axis image of the blood vessel may not be obtained. In addition, in the invention of WO2019/187649A, the blood vessel region needs to be designated by the user in order to measure the blood flow rate. Thus, there is also room for improvement in simplification of the measurement.

The present invention has been made in order to solve such a problem in the related art, and an object of the present invention is to provide an ultrasound diagnostic apparatus that can simply perform measurement while improving measurement accuracy of a blood flow rate.

In order to achieve the object, an ultrasound diagnostic apparatus according to an aspect of the present invention comprises a transducer array that acquires a reception signal by transmitting and receiving an ultrasound wave to and from a subject, a B-mode processing unit that generates a B-mode image in which at least a blood vessel is captured based on the reception signal, a display device that displays the B-mode image generated by the B-mode processing unit, a first vascular wall detection unit that detects a vascular wall in a minor axis direction by analyzing the B-mode image in which a minor axis image of the blood vessel is captured, a first blood vessel diameter calculation unit that calculates a first blood vessel diameter based on the vascular wall in the minor axis direction detected by the first vascular wall detection unit, a second vascular wall detection unit that detects a vascular wall in a major axis direction by analyzing the B-mode image in which a major axis image of the blood vessel is captured, a second blood vessel diameter calculation unit that calculates a second blood vessel diameter based on the vascular wall in the major axis direction detected by the second vascular wall detection unit, a gate setting unit that sets a Doppler gate in the blood vessel on the B-mode image in which the major axis image is captured, a Doppler processing unit that acquires Doppler data in the Doppler gate, a blood flow velocity calculation unit that calculates a blood flow velocity based on the Doppler data, and a blood flow rate measurement unit that measures a blood flow rate based on any one of the detected vascular wall in the major axis direction or the detected vascular wall in the minor axis direction and the calculated blood flow velocity, in which in a case where the second blood vessel diameter calculated by the second blood vessel diameter calculation unit is within a determined range with respect to the first blood vessel diameter calculated by the first blood vessel diameter calculation unit, the blood flow rate is automatically measured.

The second vascular wall detection unit may set a search line for searching for the vascular wall in the major axis direction on the B-mode image, and detect an anterior vascular wall and a posterior vascular wall as the vascular wall in the major axis direction based on a brightness profile of the B-mode image on the set search line.

In this case, the second vascular wall detection unit may display a detection point marker on the display device by setting the detection point marker on each of the detected anterior vascular wall and the detected posterior vascular wall.

In addition, the gate setting unit may set the Doppler gate having a center position and a size decided based on coordinates of the anterior vascular wall and the posterior vascular wall detected by the second vascular wall detection unit.

In addition, the second vascular wall detection unit may estimate a blood vessel traveling angle based on at least one of the detected anterior vascular wall or the detected posterior vascular wall and set a Doppler steer angle such that an angle correction value for the blood vessel traveling angle is within 60 degrees.

In this case, the B-mode processing unit may generate the B-mode image based on a B-mode steer angle set in accordance with the blood vessel traveling angle estimated by the second vascular wall detection unit.

In addition, the Doppler processing unit may generate a Doppler waveform image based on the Doppler data, and the display device may display both of the B-mode image generated by the B-mode processing unit and the Doppler waveform image generated by the Doppler processing unit.

Furthermore, the Doppler processing unit generates the Doppler waveform image in parallel with the generation of the B-mode image by the B-mode processing unit, and the blood flow rate is measured by the blood flow rate measurement unit by freezing both of the B-mode image and the Doppler waveform image.

Alternatively, furthermore, the Doppler processing unit generates the Doppler waveform image by acquiring the Doppler data in the Doppler gate after the B-mode image is frozen, and the blood flow rate is measured by the blood flow rate measurement unit by freezing the Doppler waveform image.

In addition, in a case where the calculated second blood vessel diameter maintains the determined range with respect to the calculated first blood vessel diameter over a determined number of frames, the blood flow rate may be automatically measured.

A control method of an ultrasound diagnostic apparatus according to another aspect of the present invention comprises generating a B-mode image in which at least a blood vessel is captured based on a reception signal obtained by transmitting and receiving an ultrasound wave to and from a subject, displaying the B-mode image, detecting a vascular wall in a minor axis direction by analyzing a minor axis image of the blood vessel captured in the B-mode image, calculating a first blood vessel diameter based on the detected vascular wall in the minor axis direction, detecting a vascular wall in a major axis direction by analyzing the B-mode image in which a major axis image of the blood vessel is captured, calculating a second blood vessel diameter based on the detected vascular wall in the major axis direction, setting, in a case where the calculated second blood vessel diameter is within a determined range with respect to the calculated first blood vessel diameter, a Doppler gate in the blood vessel on the B-mode image in which the major axis image is captured, acquiring Doppler data in the Doppler gate, calculating a blood flow velocity based on the Doppler data, and measuring a blood flow rate based on any one of the detected vascular wall in the major axis direction or the detected vascular wall in the minor axis direction and the calculated blood flow velocity.

A processor for an ultrasound diagnostic apparatus according to still another aspect of the present invention is configured to generate a B-mode image in which at least a blood vessel is captured based on a reception signal obtained by transmitting and receiving an ultrasound wave to and from a subject, display the B-mode image, detect a vascular wall in a minor axis direction by analyzing a minor axis image of the blood vessel captured in the B-mode image, calculate a first blood vessel diameter based on the detected vascular wall in the minor axis direction, detect a vascular wall in a major axis direction by analyzing the B-mode image in which a major axis image of the blood vessel is captured, calculate a second blood vessel diameter based on the detected vascular wall in the major axis direction, in a case where the calculated second blood vessel diameter is within a determined range with respect to the calculated first blood vessel diameter, set a Doppler gate in the blood vessel on the B-mode image in which the major axis image is captured, acquire Doppler data in the Doppler gate, calculate a blood flow velocity based on the Doppler data, and measure a blood flow rate based on any one of the detected vascular wall in the major axis direction or the detected vascular wall in the minor axis direction and the calculated blood flow velocity.

According to the present invention, the ultrasound diagnostic apparatus comprises the first vascular wall detection unit that detects the vascular wall in the minor axis direction by analyzing the B-mode image in which the minor axis image of the blood vessel is captured, the first blood vessel diameter calculation unit that calculates the first blood vessel diameter based on the vascular wall in the minor axis direction, the second vascular wall detection unit that detects the vascular wall in the major axis direction by analyzing the B-mode image in which the major axis image of the blood vessel is captured, the second blood vessel diameter calculation unit that calculates the second blood vessel diameter based on the vascular wall in the major axis direction, the gate setting unit that sets the Doppler gate in the blood vessel on the B-mode image in which the major axis image is captured, the Doppler processing unit that acquires the Doppler data in the Doppler gate, the blood flow velocity calculation unit that calculates the blood flow velocity based on the Doppler data, and the blood flow rate measurement unit that measures the blood flow rate based on any one of the vascular wall in the major axis direction or the vascular wall in the minor axis direction and the blood flow velocity, in which in a case where the second blood vessel diameter calculated by the second blood vessel diameter calculation unit is within the determined range with respect to the first blood vessel diameter calculated by the first blood vessel diameter calculation unit, the blood flow rate is automatically measured. Thus, it is possible to simply perform the measurement while improving measurement accuracy of the blood flow rate.

DESCRIPTION OF THE PREFERRED EMBODIMENTS

Hereinafter, embodiments of the invention will be described with reference to the accompanying drawings.

The description of configuration requirements described below is provided based on the representative embodiment of the present invention, but the present invention is not limited to such an embodiment.

In the present specification, a numerical range represented using "to" means a range including the numerical values before and after "to" as a lower limit value and an upper limit value.

In addition, in the present specification, the terms "perpendicular" and "parallel" include a range of errors allowed in the technical field to which the present invention belongs. For example, the terms "perpendicular" and "parallel" mean a range less than ±10 degrees with respect to strict perpendicularity or parallelism, and the error with respect to the strict perpendicularity or parallelism is preferably less than or equal to 5 degrees, and more preferably less than or equal to 3 degrees.

In the present specification, the terms "identical" and "same" include an error range generally allowed in the technical field. In addition, in the present specification, in a case of referring to "all", "any", or "whole surface", the term includes an error range generally allowed in the technical field in addition to a case of 100%, and includes, for example, a case of greater than or equal to 99%, a case of greater than or equal to 95%, or a case of greater than or equal to 90%.

First Embodiment

Figure 1:
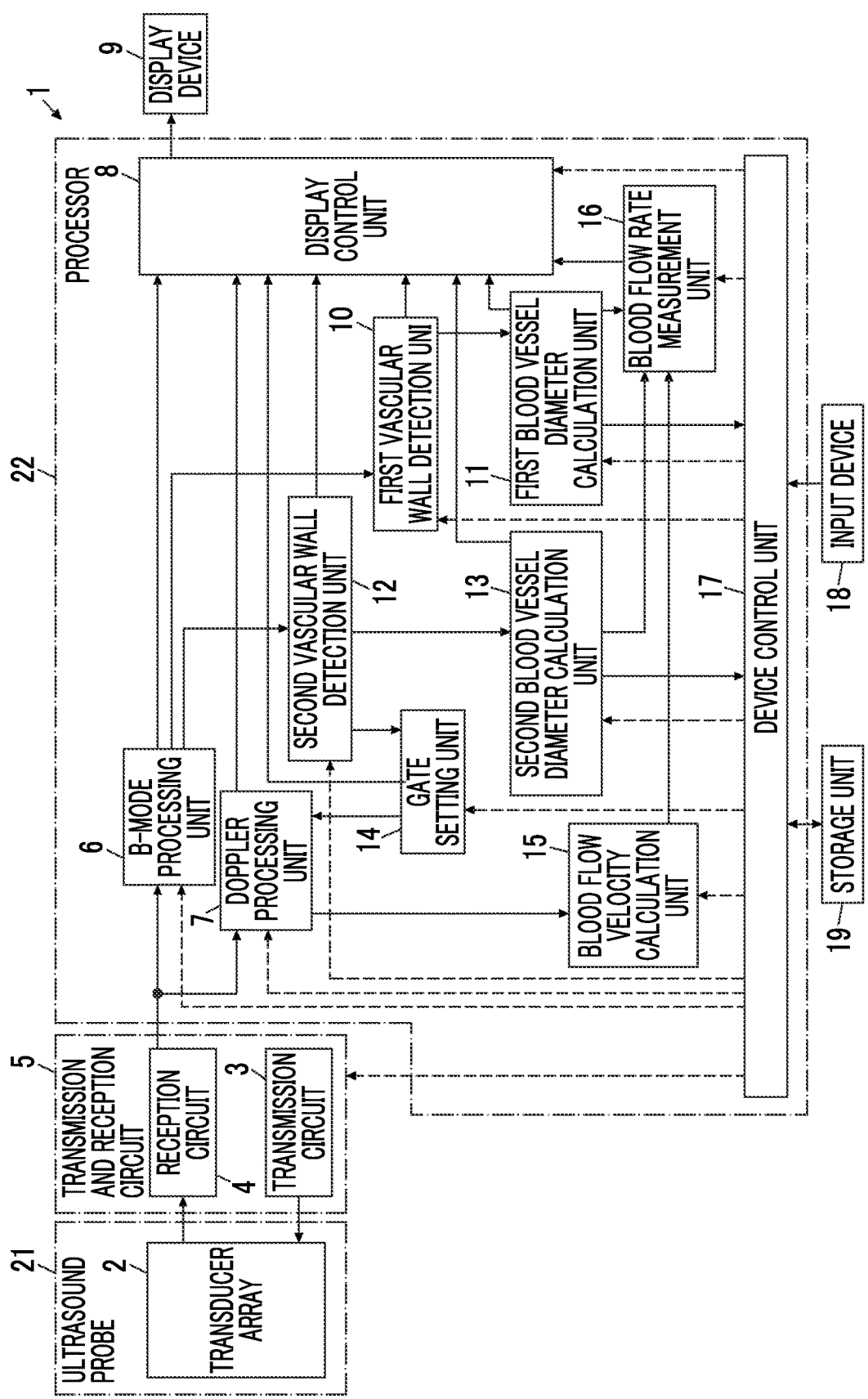
FIG. 1 is a block diagram illustrating a configuration of an ultrasound diagnostic apparatus according to a first embodiment of the present invention.

FIG. 1 illustrates a configuration of an ultrasound diagnostic apparatus 1 according to a first embodiment of the present invention. As illustrated in FIG. 1, the ultrasound diagnostic apparatus 1 comprises a transducer array 2, and each of a transmission circuit 3 and a reception circuit 4 is connected to the transducer array 2. Here, the transmission circuit 3 and the reception circuit 4 constitute a transmission and reception circuit 5. A brightness mode (B-mode) processing unit 6 and a Doppler processing unit 7 are connected to the reception circuit 4, and a display device 9 is connected to the B-mode processing unit 6 and the Doppler processing unit 7 via a display control unit 8.

In addition, a first vascular wall detection unit 10 is connected to the B-mode processing unit 6, and a first blood vessel diameter calculation unit 11 is connected to the first vascular wall detection unit 10. In addition, a second vascular wall detection unit 12 is connected to the B-mode processing unit 6, and a second blood vessel diameter calculation unit 13 and a gate setting unit 14 are connected to the second vascular wall detection unit 12. The gate setting unit 14 is connected to the Doppler processing unit 7. In addition, a blood flow velocity calculation unit 15 is connected to the Doppler processing unit 7. In addition, a blood flow rate measurement unit 16 is connected to the first blood vessel diameter calculation unit 11, the second blood vessel diameter calculation unit 13, and the blood flow velocity calculation unit 15. In addition, the first vascular wall detection unit 10, the first blood vessel diameter calculation unit 11, the second vascular wall detection unit 12, the second blood vessel diameter calculation unit 13, the gate setting unit 14, and the blood flow rate measurement unit 16 are connected to the display control unit 8.

In addition, a device control unit 17 is connected to the transmission and reception circuit 5, the B-mode processing unit 6, the Doppler processing unit 7, the display control unit 8, the first vascular wall detection unit 10, the first blood vessel diameter calculation unit 11, the second vascular wall detection unit 12, the second blood vessel diameter calculation unit 13, the gate setting unit 14, the blood flow velocity calculation unit 15, and the blood flow rate measurement unit 16. In addition, an input device 18 and a storage unit 19 are connected to the device control unit 17. The device control unit 17 and the storage unit 19 are connected so as to exchange information bidirectionally.

In addition, the transducer array 2 is included in an ultrasound probe 21. In addition, the B-mode processing unit 6, the Doppler processing unit 7, the display control unit 8, the first vascular wall detection unit 10, the first blood vessel diameter calculation unit 11, the second vascular wall detection unit 12, the second blood vessel diameter calculation unit 13, the gate setting unit 14, the blood flow velocity calculation unit 15, and the blood flow rate measurement unit 16 constitute a processor 22 for the ultrasound diagnostic apparatus 1.

The transducer array 2 of the ultrasound probe 21 illustrated in FIG. 1 has a plurality of transducers arranged in a one-dimensional or two-dimensional manner. Each of the transducers transmits an ultrasound wave, receives an ultrasound echo from a subject, and outputs a signal based on the ultrasound echo in accordance with a drive signal supplied from the transmission circuit 3. For example, each transducer is configured by forming electrodes at both ends of a piezoelectric body consisting of piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

The transmission circuit 3 includes, for example, a plurality of pulse generators, and adjusts an amount of delay of each drive signal to form an ultrasound beam with ultrasound waves transmitted from the plurality of transducers of the transducer array 2 based on a transmission delay pattern selected in accordance with a control signal from the device control unit 17 and supplies the adjusted drive signals to the plurality of transducers. Thus, in a case where a pulsed or continuous-wave voltage is applied to the electrodes of the transducers of the transducer array 2, the piezoelectric body expands and contracts to generate pulsed or continuous-wave ultrasound waves from each transducer. The ultrasound beam is formed from a combined wave of these ultrasound waves.

The transmitted ultrasound beam is reflected by a target, for example, a site of the subject, and propagates toward the transducer array 2 of the ultrasound probe 21. The ultrasound waves propagating toward the transducer array 2 in this manner are received by each transducer constituting the transducer array 2. In this case, each transducer constituting the transducer array 2 expands and contracts by receiving the propagating ultrasound echo to generate electrical signals, and outputs the electrical signals to the reception circuit 4.

Figure 2:
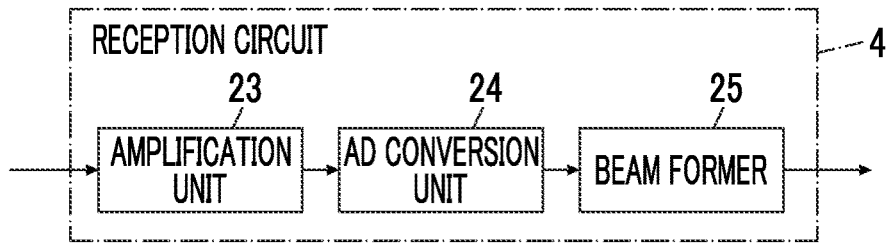
FIG. 2 is a block diagram illustrating an internal configuration of a reception circuit in the first embodiment of the present invention.

The reception circuit 4 processes the signals output from the transducer array 2 in accordance with the control signal from the device control unit 17 to generate reception data, which is so-called radio frequency (RF) data. As illustrated in FIG. 2, the reception circuit 4 has a configuration in which an amplification unit 23, an analog digital (AD) conversion unit 24, and a beam former 25 are connected in series.

The amplification unit 23 amplifies the signals input from each transducer constituting the transducer array 2, and transmits the amplified signals to the AD conversion unit 24. The AD conversion unit 24 converts the signals transmitted from the amplification unit 23 into digital data, and transmits the data to the beam former 25. The beam former 25 performs so-called reception focusing processing by applying a delay of each data to each data converted by the AD conversion unit 24 and adding each data in accordance with a sound speed set based on a reception delay pattern selected in accordance with the control signal from the device control unit 17 or a distribution of the sound speed. Through the reception focusing processing, reception data in which each data converted by the AD conversion unit 24 is phased and added and a focus of the ultrasound echo is narrowed is acquired.

Figure 3:
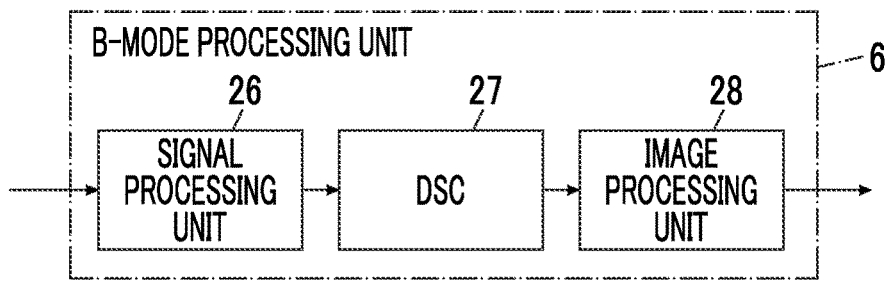
FIG. 3 is a block diagram illustrating an internal configuration of a B-mode processing unit in the first embodiment of the present invention.

As illustrated in FIG. 3, the B-mode processing unit 6 has a configuration in which a signal processing unit 26, a digital scan converter (DSC) 27, and an image processing unit 28 are sequentially connected in series.

The signal processing unit 26 generates a B-mode image signal that is tomographic image information related to tissues inside the subject, by correcting attenuation by distance in accordance with depths of reflection positions of the ultrasound waves and then, performing envelope detection processing on the reception data generated by the reception circuit 4.

The DSC 27 converts (raster conversion) the B-mode image signal generated by the signal processing unit 26 into an image signal complying with a normal television signal scanning method.

The image processing unit 28 performs various kinds of necessary image processing such as gradation processing on the B-mode image signal input from the DSC 27 and then, outputs the B-mode image signal to the display control unit 8. Hereinafter, the B-mode image signal subjected to the image processing by the image processing unit 28 will be simply referred to as a B-mode image.

In a case where the B-mode image generated by the B-mode processing unit 6 includes a minor axis image of a blood vessel of the subject, the first vascular wall detection unit 10 detects a vascular wall in a minor axis direction by analyzing the minor axis image of the blood vessel captured in the B-mode image. Here, the minor axis image of the blood vessel refers to a lateral cross section of the blood vessel along a direction orthogonal to a traveling direction of the blood vessel.

Figure 4:
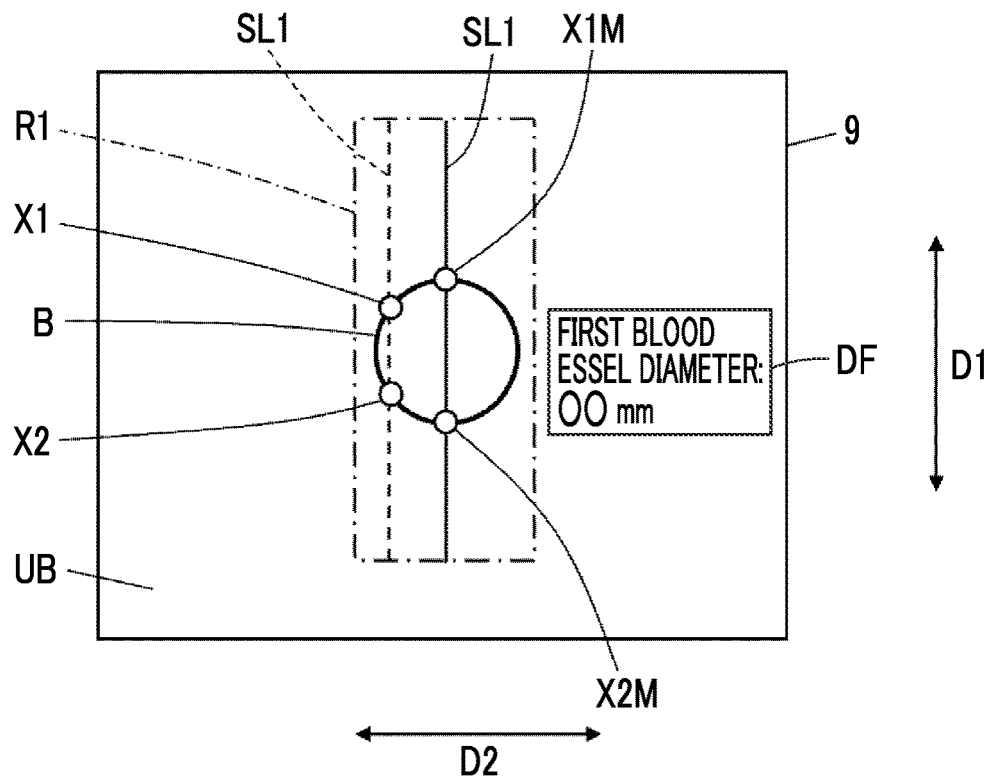
FIG. 4 is a diagram schematically illustrating an example of a B-mode image representing a minor axis image of a blood vessel.
Figure 5:
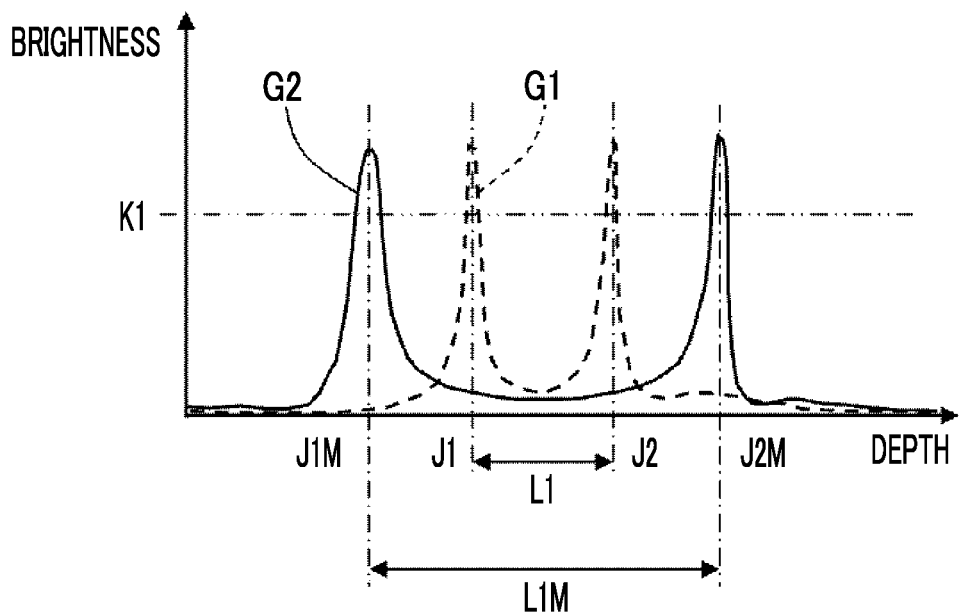
FIG. 5 is a diagram schematically illustrating an example of a brightness profile of an image on a straight line crossing the minor axis image of the blood vessel.

In detecting the vascular wall in the minor axis direction, for example, as illustrated in FIG. 4, the first vascular wall detection unit 10 sets a search region R1 of a blood vessel B in a center portion in an azimuthal direction, that is, a lateral direction D2, orthogonal to a depth direction D1 of a B-mode image UB and creates a brightness profile of the image along a search line SL1 in the search region R1 by detecting brightness on the search line SL1 while scanning the virtual search line SL1 extending along the depth direction D1 of the B-mode image UB in the lateral direction D2 in the set search region R1. For example, as illustrated in FIG. 5, the brightness profile of the image represents a relationship between a depth in the B-mode image UB and the brightness of the image on the search line SL1. In the example illustrated in FIG. 5, the depth is plotted on a horizontal axis, and the brightness is plotted on a vertical axis.

In FIG. 4, the search line SL1 of a dotted line passing through a location relatively separated from a center of the blood vessel B on the minor axis image of the blood vessel B and the search line SL of a solid line passing through near the center of the blood vessel B are illustrated as examples of the search line SL1. In addition, in FIG. 5, a graph G1 of a dotted line corresponding to the search line SL1 of the dotted line and a graph G2 of a solid line corresponding to the search line SL1 of the solid line are illustrated as examples of the brightness profile.

Here, a brightness change of the image on the search line SL1 passing through the minor axis image of the blood vessel B is greater at two points X1 and X2 corresponding to the vascular wall than at the other points on the search line SL1. Thus, for example, in the brightness profile in FIG. 5, two depths J1 and J2 at which a brightness value is the maximal value greater than a constant brightness threshold value K1 correspond to the two points X1 and X2 corresponding to the vascular wall. In addition, in a case where the search line SL1 is scanned in the lateral direction D2 on the minor axis image of the blood vessel B having an approximately circular shape, for example, a value of a difference L1 between the depth J1 and the depth J2 in the brightness profile is increased to the maximum value corresponding to a diameter of the blood vessel B from zero and then, is further decreased to zero in accordance with the scanning of the search line SL1 from one end to the other end of the minor axis image of the blood vessel B in the lateral direction D2. The value of the difference L1 calculated while the search line SL1 is scanned on the minor axis image of the blood vessel B in the lateral direction D2 changes to have the maximal value.

Thus, the first vascular wall detection unit 10 can determine whether or not the minor axis image of the blood vessel is included in the B-mode image UB based on the brightness profile created while the search line SL1 is scanned in the lateral direction D2. For example, the first vascular wall detection unit 10 calculates the difference L1 between the depth J1 and the depth J2 in the brightness profile while scanning the search line SL1 in the lateral direction D2 and, in a case where the value of the calculated difference L1 changes to have the maximal value, can recognize that the minor axis image of the blood vessel B is present in the search region R1 of the B-mode image UB. In this case, the first vascular wall detection unit 10 detects trajectories of the points X1 and X2 corresponding to the depths J1 and J2 at which the brightness value is the maximum in the brightness profile as the vascular wall. In addition, the first vascular wall detection unit 10 detects information of positions of points X1M and X2M corresponding to depths J1M and J2M at which the difference L1 calculated while the search line SL1 is scanned in the lateral direction D2 is a maximum value L1M, and transmits the information to the first blood vessel diameter calculation unit 11. The points X1M and X2M correspond to intersections between the search line SL1 passing through the center of the blood vessel B and contours of the minor axis image of the blood vessel B.

The first blood vessel diameter calculation unit 11 calculates a first blood vessel diameter corresponding to the diameter of the blood vessel B based on the information of the positions of the points X1M and X2M on the vascular wall received from the first vascular wall detection unit 10. For example, as illustrated in FIG. 4, the first blood vessel diameter calculation unit 11 can display a calculated first blood vessel diameter DF on the display device 9.

The second vascular wall detection unit 12 detects a vascular wall in a major axis direction by analyzing the B-mode image UB that is generated based on the first blood vessel diameter DF calculated by the first blood vessel diameter calculation unit 11 and in which a major axis image of the blood vessel B is captured. Here, the major axis image of the blood vessel B refers to a longitudinal cross section of the blood vessel B along the traveling direction of the blood vessel B.

Figure 6:
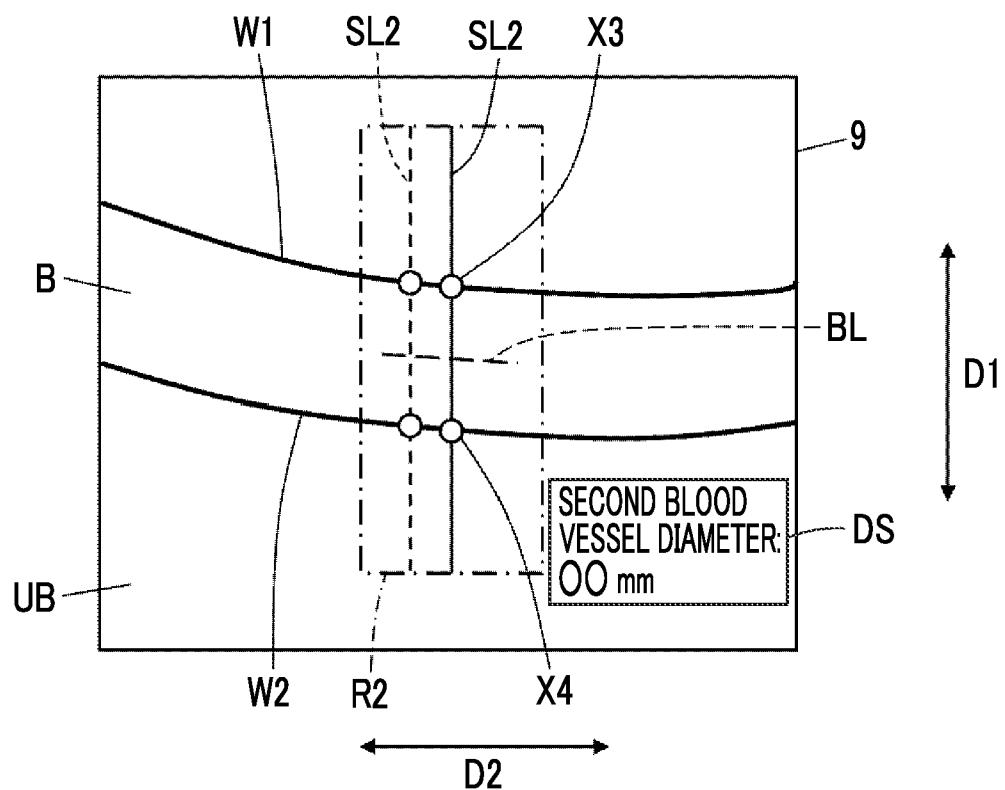
FIG. 6 is a diagram schematically illustrating an example of a B-mode image representing a major axis image of the blood vessel.
Figure 7:
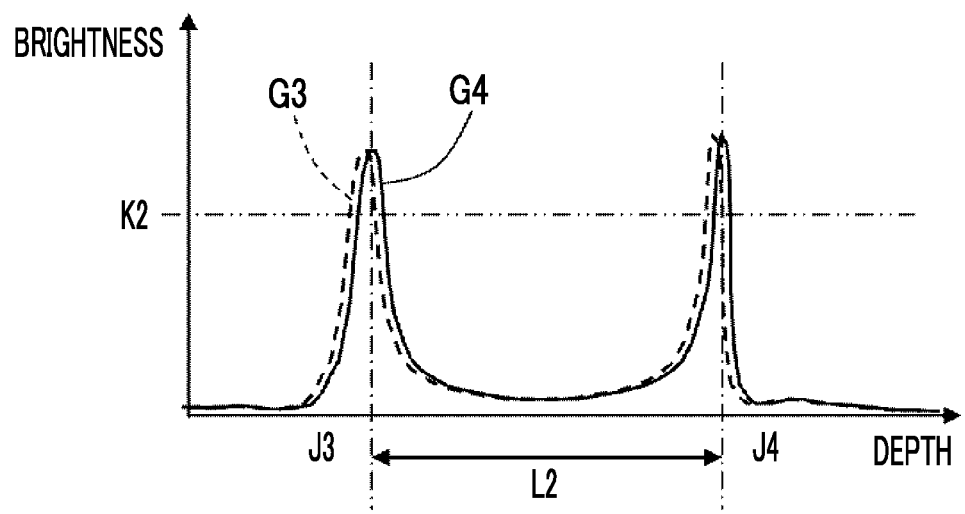
FIG. 7 is a diagram schematically illustrating an example of a brightness profile of an image on a straight line crossing the major axis image of the blood vessel.

In detecting the vascular wall in the major axis direction, for example, as illustrated in FIG. 6, the second vascular wall detection unit 12 sets a search region R2 in a center portion in the lateral direction D2 of the B-mode image UB and creates a brightness profile of the image along a search line SL2 as illustrated in FIG. 7 by detecting the brightness on the search line SL2 while scanning the virtual search line SL2 extending along the depth direction D1 in the lateral direction D2 in the set search region R2.

In FIG. 6, the search line SL2 of a dotted line and the search line SL2 of a solid line arranged at a different position from the search line SL2 are illustrated as examples of the search line SL2. In addition, in FIG. 7, a graph G3 of a dotted line corresponding to the search line SL2 of the dotted line and a graph G4 of a solid line corresponding to the search line SL2 of the solid line are illustrated as examples of the graph of the brightness profile. While the graph G3 and the graph G4 are shifted from each other in a direction parallel to the horizontal axis, a difference in depth between two points at which the brightness is the maximum is almost identical between each other.

Here, a brightness change of the image on the search line SL2 passing through the major axis image of the blood vessel B is greater at two points X3 and X4 corresponding to the vascular wall than at the other points on the search line SL2, in the same manner as the brightness change of the image on the search line SL1 passing through the minor axis image of the blood vessel B. Thus, for example, in the brightness profile in FIG. 7, two depths J3 and J4 at which the brightness value is the maximal value greater than a constant brightness threshold value K2 correspond to the two points X3 and X4 corresponding to the vascular wall. In addition, as illustrated in FIG. 6, in a case where the search line SL2 is scanned in the lateral direction D2 on the major axis image of the blood vessel B of a tubular shape extending approximately along the lateral direction D2, a difference L2 between the depth J3 and the depth J4 in the brightness profile ideally does not change even in a case where the search line SL2 is scanned in the lateral direction D2. Even in a case where the difference L2 changes, a width of change is small.

Thus, the second vascular wall detection unit 12 can determine whether or not the major axis image of the blood vessel B is included in the B-mode image UB based on the brightness profile created by scanning the search line SL2 in the lateral direction D2. For example, the second vascular wall detection unit 12 calculates the difference L2 between the depth J3 and the depth J4 in the brightness profile by scanning the search line SL2 in the lateral direction D2 and, in a case where a value of the calculated difference L2 is almost constant, can determine that the major axis image of the blood vessel B is present in the search region R2 of the B-mode image UB. Here, for example, the value of the difference L2 being almost constant means that a difference between the maximum value and the minimum value of the difference L2 is less than or equal to a constant value.

In addition, the second vascular wall detection unit 12 detects a position of the relatively shallow depth J3 out of the detected depths J3 and J4 at which the brightness value is the maximal value, as a position of an anterior vascular wall W1 and detects a position of the relatively deep depth J4 as a position of a posterior vascular wall W2. In addition, the second vascular wall detection unit 12 transmits information of the detected positions of the anterior vascular wall W1 and the posterior vascular wall W2 to the second blood vessel diameter calculation unit 13.

The second blood vessel diameter calculation unit 13 calculates a second blood vessel diameter of the blood vessel B based on the information of the positions of the anterior vascular wall W1 and the posterior vascular wall W2 detected by the second vascular wall detection unit 12. For example, the second blood vessel diameter calculation unit 13 calculates the maximum distance among distances between the anterior vascular wall W1 and the posterior vascular wall W2 in the depth direction D1 as the second blood vessel diameter. As illustrated in FIG. 6, the second vascular wall detection unit 12 displays a calculated second blood vessel diameter DS on the display device 9.

In addition, the second blood vessel diameter calculation unit 13 determines whether or not the second blood vessel diameter DS has a value within a determined range including the first blood vessel diameter DF by comparing the calculated second blood vessel diameter DS with the first blood vessel diameter DF calculated by the first blood vessel diameter calculation unit 11. In a case where it is determined that the second blood vessel diameter DS has a value within the determined range, the second blood vessel diameter calculation unit 13 determines that the B-mode image UB including the major axis image of the blood vessel B representing the longitudinal cross section passing through the center of the blood vessel B is obtained, and transmits the value of the second blood vessel diameter DS within the determined range to the blood flow rate measurement unit 16.

The second vascular wall detection unit 12 estimates a blood vessel traveling angle in the B-mode image UB. For example, the second vascular wall detection unit 12 can estimate an inclination of the blood vessel B by estimating a straight line passing through a plurality of positions on the detected anterior vascular wall W1 and a straight line passing through a plurality of positions on the detected posterior vascular wall W2 and averaging inclinations of the two estimated straight lines. In the example illustrated in FIG. 6, a virtual blood vessel gradient line BL representing a gradient of the blood vessel B is obtained. In addition, the second vascular wall detection unit 12 may estimate the inclination of the blood vessel B based on any of the straight line passing through the plurality of positions on the detected anterior vascular wall W1 or the straight line passing through the plurality of positions on the detected posterior vascular wall W2.

Figure 8:
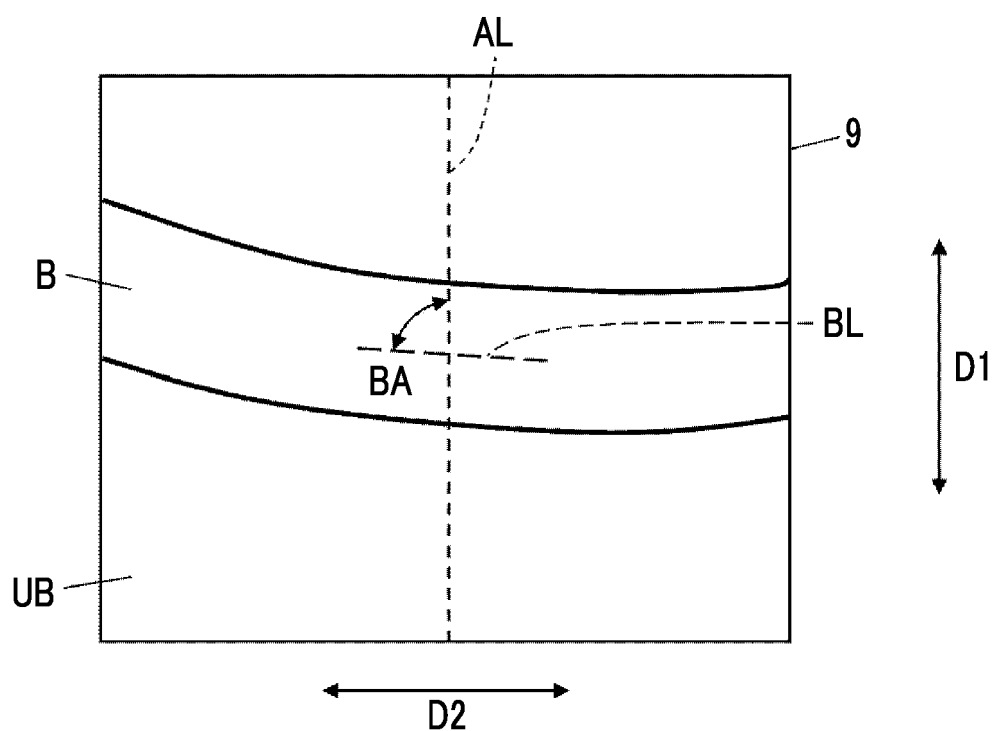
FIG. 8 is a diagram schematically illustrating an estimated traveling angle of the blood vessel on the B-mode image.

In addition, for example, as illustrated in FIG. 8, the second vascular wall detection unit 12 can estimate an angle between the obtained blood vessel gradient line BL and a virtual straight line AL along the depth direction D1 of the B-mode image UB as a blood vessel traveling angle BA.

Figure 9:
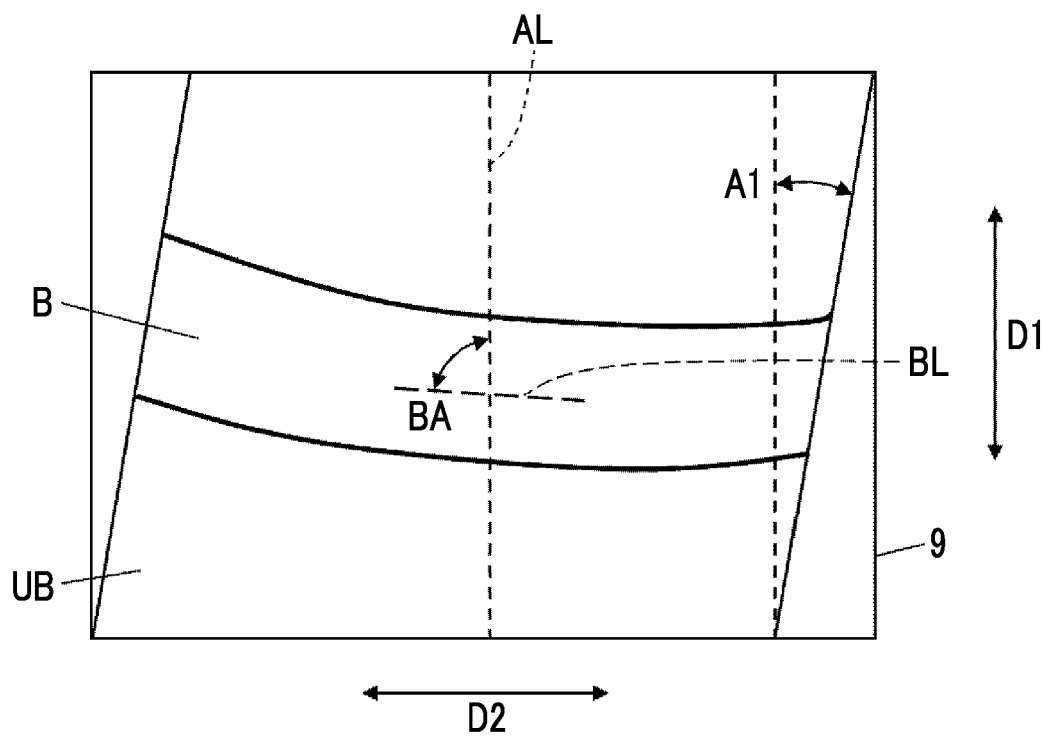
FIG. 9 is a diagram schematically illustrating a method of setting a B-mode steer angle in the first embodiment of the present invention.

In addition, the second vascular wall detection unit 12 sets a B-mode steer angle using the estimated blood vessel traveling angle BA. For example, as illustrated in FIG. 9, an angle A1 or the like is set as the B-mode steer angle. The B-mode steer angle is defined as an angle between a scan line in the generation of the B-mode image UB by the B-mode processing unit 6 and the straight line AL along the depth direction D1 in the B-mode image UB. Here, in order to obtain the B-mode image UB in which the anterior vascular wall W1 and the posterior vascular wall W2 are clearly captured, the second vascular wall detection unit 12 sets the B-mode steer angle such that the angle between the scan line in the generation of the B-mode image UB and the blood vessel gradient line BL is approximated to 90 degrees.

For example, the second vascular wall detection unit 12, using the blood vessel traveling angle BA, the determined angle A1, and a determined angle A2 greater than the angle A1, can set the B-mode steer angle to 0 degrees in a case where a relationship of 90−BA<A1/2 is satisfied, set the B-mode steer angle to the angle A1 as illustrated in FIG. 9 in a case where a relationship of A1/2≤90−BA<A2/2 is satisfied, and set the B-mode steer angle to the angle A2 in a case where a relationship of A2/2≤90−BA is satisfied. Here, for example, the angle A1 can be set to 7.5 degrees in advance, and the angle A2 can be set to 15 degrees in advance.

Figure 10:
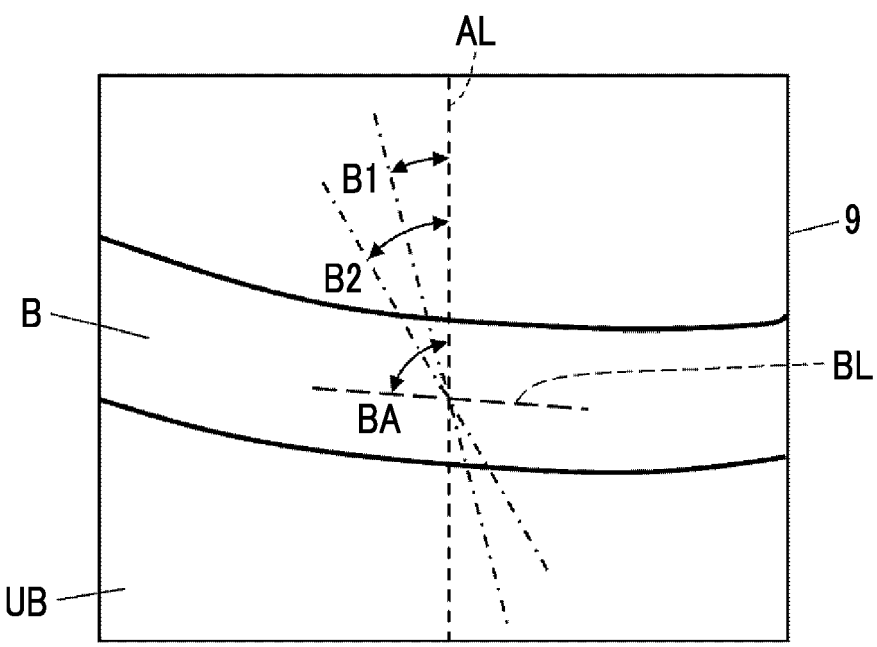
FIG. 10 is a diagram schematically illustrating a method of setting a Doppler steer angle in the first embodiment of the present invention.

In addition, the second vascular wall detection unit 12 sets a Doppler steer angle using the estimated blood vessel traveling angle BA. For example, as illustrated in FIG. 10, an angle B1, an angle B2, or the like is set as the Doppler steer angle. Here, the Doppler steer angle refers to an inclination angle of the scan line in obtaining Doppler data.

Figure 11:
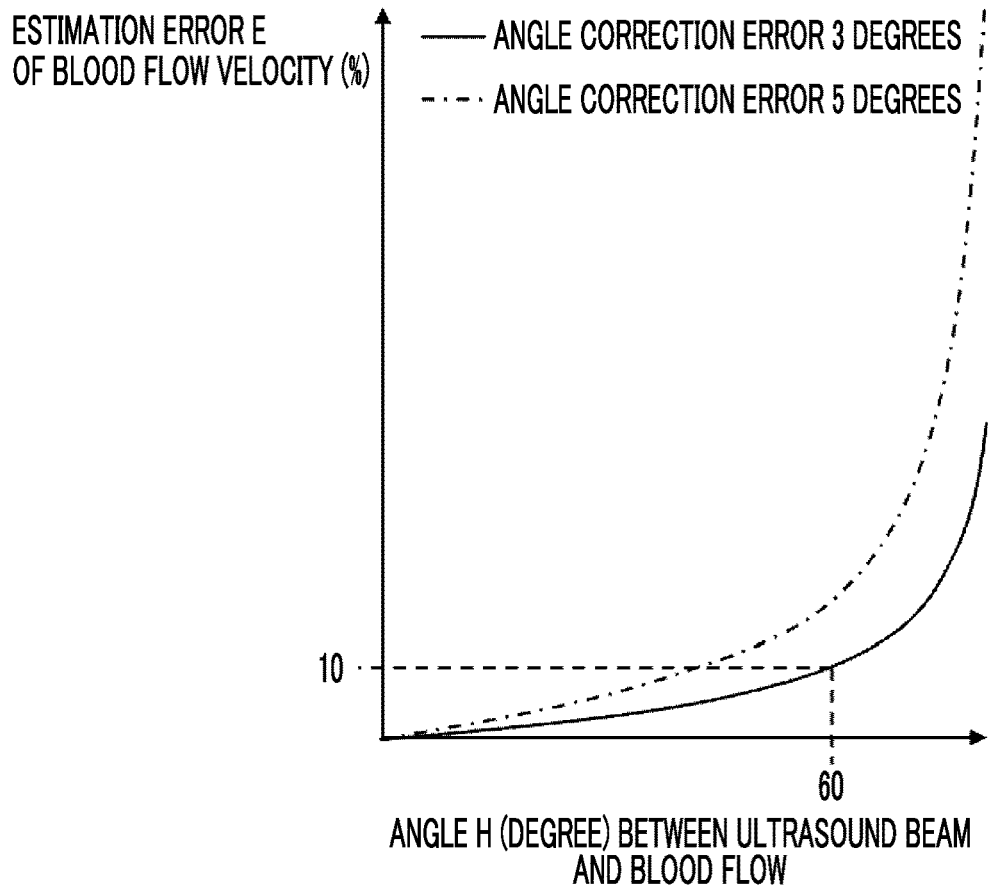
FIG. 11 is a graph illustrating a relationship between an angle between an ultrasound beam and a blood flow and an estimation error of a blood flow velocity.

Here, it is known that an angle H between the ultrasound beam transmitted toward the blood vessel B for acquiring the Doppler data and the blood flow in the blood vessel B, and an estimation error E of the blood flow velocity calculated based on the acquired Doppler data have a relationship illustrated in FIG. 11. According to the relationship, it is perceived that as the angle H of the ultrasound beam with respect to the blood flow is increased, the estimation error E of the blood flow velocity is exponentially increased. In addition, it is perceived that as an error of angle correction for the blood vessel traveling angle is increased, the estimation error E of the blood flow velocity is increased.

In addition, regarding the angle H between the ultrasound beam and the blood flow and the estimation error E of the blood flow velocity, it is known that, for example, in a case where the angle H between the ultrasound beam and the blood flow is maintained within 60 degrees, the estimation error E of the blood flow velocity falls within 10% even in a case where there is an error of 3 degrees in the angle correction for the blood vessel traveling angle, and the blood flow velocity can be accurately obtained. Therefore, in order to accurately calculate the blood flow velocity, the second vascular wall detection unit 12 sets the Doppler steer angle such that an angle correction value for the blood vessel traveling angle BA, that is, an angle between the scan line and the blood vessel gradient line BL, is within 60 degrees.

For example, the second vascular wall detection unit 12, using the blood vessel traveling angle BA, the determined angle B1, and the angle B2 greater than the angle B1 as illustrated in FIG. 10, can set the Doppler steer angle to 0 degrees in a case where a relationship of BA<60 is satisfied, set the Doppler steer angle to the angle B1 in a case where a relationship of 60≤BA<60+B1 is satisfied, and set the Doppler steer angle to the angle B2 in a case where a relationship of 60+B1≤BA is satisfied. Here, for example, the angle B1 can be set to 15 degrees in advance, and the angle B2 can be set to 30 degrees in advance.

Figure 12:
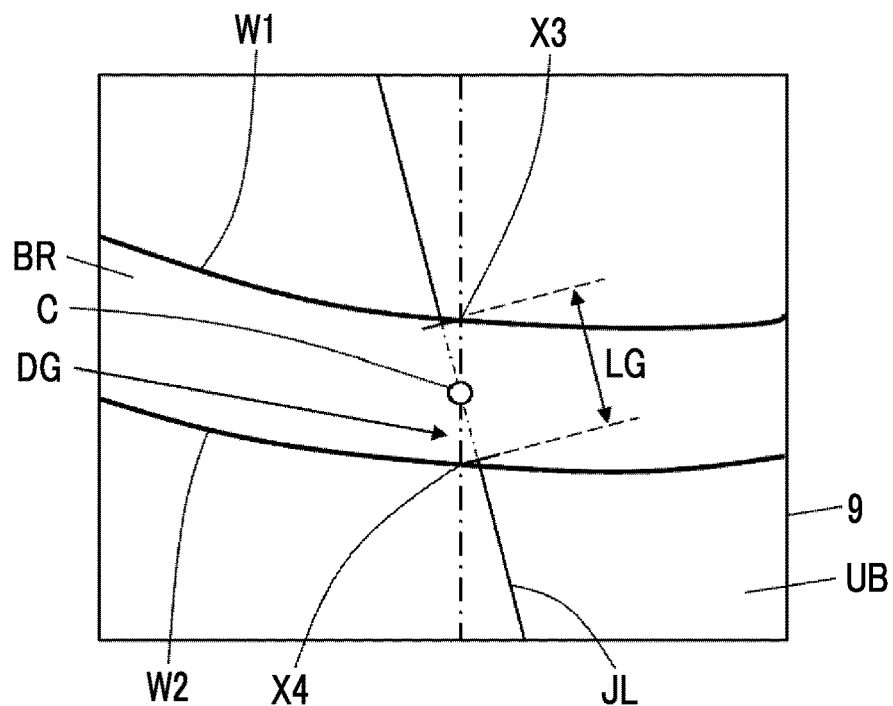
FIG. 12 is a diagram schematically illustrating the B-mode image displayed on a display device and a Doppler gate set on the B-mode image in the first embodiment of the present invention.

As illustrated in FIG. 12, the gate setting unit 14 sets a Doppler gate DG having a center position and a size decided based on coordinates of the anterior vascular wall W1 and coordinates of the posterior vascular wall W2 detected by the second vascular wall detection unit 12, in the blood vessel region BR on the B-mode image UB. In this case, the gate setting unit 14 can set, as the center position of the Doppler gate DG, a midpoint C between positions of the two points X3 and X4 detected as the position of the anterior vascular wall W1 and the position of the posterior vascular wall W2 by the second vascular wall detection unit 12, and set the Doppler gate DG on a virtual straight line JL that passes through the midpoint C and is inclined with respect to the depth direction D1 by the set Doppler steer angle.

The straight line JL corresponds to the scan line. In addition, the gate setting unit 14 can set a length calculated by multiplying the second blood vessel diameter DS calculated by the second vascular wall detection unit 12 by a determined value, as a gate width LG of the Doppler gate DG. Here, the determined value by which the second blood vessel diameter DS is multiplied is a number such as 0.75 that is greater than 0 and less than or equal to 1.00, and for example, is decided by an input operation of the user through the input device 18.

In addition, as illustrated in FIG. 12, the gate setting unit 14 displays the set Doppler gate DG on the display device 9 in a superimposed manner on the B-mode image UB.

Figure 13:
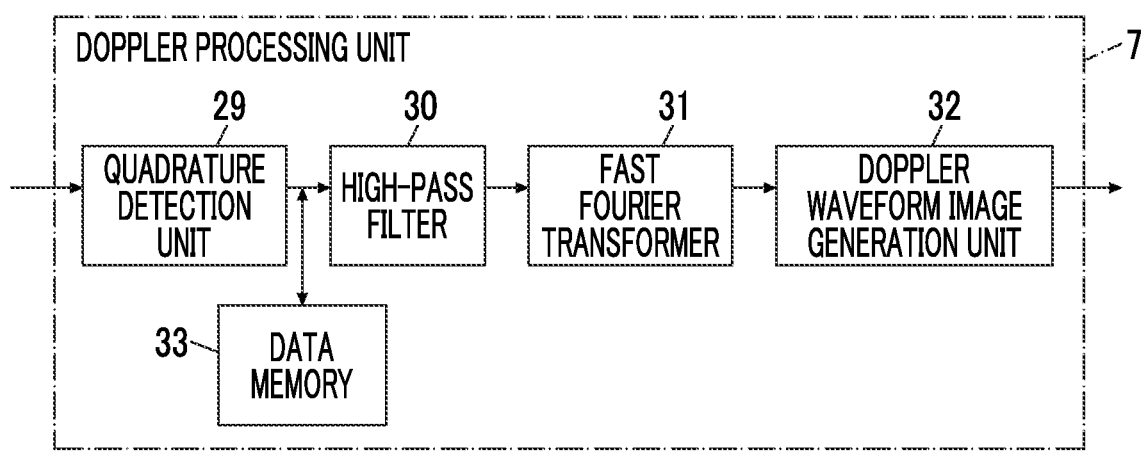
FIG. 13 is a block diagram illustrating an internal configuration of a Doppler processing unit in the first embodiment of the present invention.

The Doppler processing unit 7 acquires the Doppler data in the Doppler gate DG set in the blood vessel region BR by the gate setting unit 14, and generates a Doppler waveform image based on the acquired Doppler data. As illustrated in FIG. 13, the Doppler processing unit 7 has a configuration in which a quadrature detection unit 29, a high-pass filter 30, a fast Fourier transformer 31, and a Doppler waveform image generation unit 32 are sequentially connected in series and a data memory 33 is connected to an output terminal of the quadrature detection unit 29.

The quadrature detection unit 29 performs quadrature detection on the reception data by mixing the reception data generated by the reception circuit 4 with a carrier signal having a reference frequency and converts the reception data into complex data.

The high-pass filter 30 functions as a so-called wall filter, and removes a frequency component originating from a motion of a body tissue inside the subject, from the complex data generated by the quadrature detection unit 29.

The fast Fourier transformer 31 obtains the blood flow velocity by frequency analysis by performing a Fourier transform on the complex data of a plurality of sample points and generates spectrum signals.

The Doppler waveform image generation unit 32 generates a Doppler waveform image signal by aligning the spectrum signals generated by the fast Fourier transformer 31 on a time axis and representing a magnitude of each frequency component in brightness. Hereinafter, the Doppler waveform image signal generated by the Doppler waveform image generation unit 32 will be simply referred to as the Doppler waveform image.

In addition, the data memory 33 stores the complex data converted from the reception data by the quadrature detection unit 29.

The blood flow velocity calculation unit 15 calculates the blood flow velocity using a so-called pulse Doppler method based on the Doppler data acquired by the Doppler processing unit 7. The blood flow velocity calculation unit 15 can calculate an average blood flow velocity in each heartbeat period.

The blood flow rate measurement unit 16, assuming that the blood vessel has a circular cross section, calculates a cross-sectional area of the blood vessel B based on the second blood vessel diameter DS that is calculated by the second blood vessel diameter calculation unit 13 and corresponds to the diameter of the blood vessel B. In addition, the blood flow rate measurement unit 16 measures a blood flow rate representing a volume of blood flowing in the blood vessel B per unit time based on the calculated cross-sectional area of the blood vessel B and the blood flow velocity calculated by the blood flow velocity calculation unit 15.

The device control unit 17 controls each unit of the ultrasound diagnostic apparatus 1 based on a program stored in advance in the storage unit 19 or the like and the input operation of the user through the input device 18.

The display control unit 8 performs predetermined processing on the B-mode image UB generated by the B-mode processing unit 6, the Doppler waveform image generated by the Doppler processing unit 7, and the like and displays the B-mode image UB, the Doppler waveform image, and the like on the display device 9 under control of the device control unit 17.

The display device 9 displays the B-mode image UB, the Doppler waveform image, and the like under control of the display control unit 8, and for example, includes a display device such as a liquid crystal display (LCD) or an organic electroluminescence (EL) display.

The input device 18 is used by the user to perform the input operation, and can be configured to comprise a keyboard, a mouse, a trackball, a touchpad, a touch panel, and the like.

The storage unit 19 stores an operation program and the like of the ultrasound diagnostic apparatus 1, and recording media such as a flash memory, a hard disk drive (HDD), a solid state drive (SSD), a flexible disk (FD), a magneto-optical disc (MO disc), a magnetic tape (MT), a random access memory (RAM), a compact disc (CD), a digital versatile disc (DVD), a secure digital card (SD card), and a universal serial bus memory (USB memory), a server, or the like can be used.

The processor 22 having the B-mode processing unit 6, the Doppler processing unit 7, the display control unit 8, the first vascular wall detection unit 10, the first blood vessel diameter calculation unit 11, the second vascular wall detection unit 12, the second blood vessel diameter calculation unit 13, the gate setting unit 14, the blood flow velocity calculation unit 15, the blood flow rate measurement unit 16, and the device control unit 17 is configured with a central processing unit (CPU) and a control program causing the CPU to perform various kinds of processing. The processor 22 may be configured using a field programmable gate array (FPGA), a digital signal processor (DSP), an application specific integrated circuit (ASIC), a graphics processing unit (GPU), or other integrated circuits (IC) or may be configured with a combination thereof.

In addition, the B-mode processing unit 6, the Doppler processing unit 7, the display control unit 8, the first vascular wall detection unit 10, the first blood vessel diameter calculation unit 11, the second vascular wall detection unit 12, the second blood vessel diameter calculation unit 13, the gate setting unit 14, the blood flow velocity calculation unit 15, the blood flow rate measurement unit 16, and the device control unit 17 of the processor 22 can be configured to be partially or entirely integrated into one CPU or the like.

Figure 14:
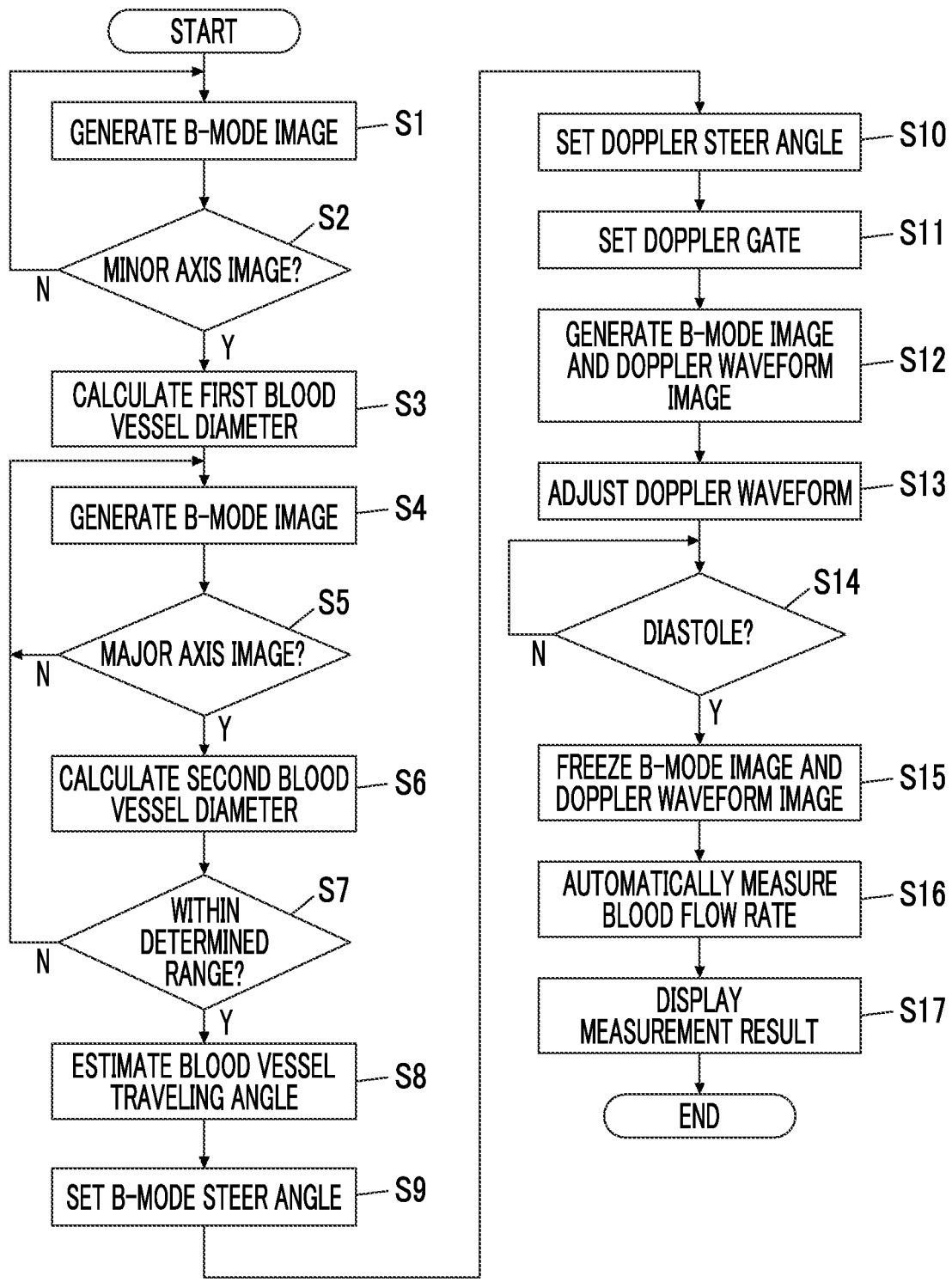
FIG. 14 is a flowchart illustrating an operation of the ultrasound diagnostic apparatus according to the first embodiment of the present invention.

Hereinafter, an operation of the ultrasound diagnostic apparatus 1 in the first embodiment will be described in detail using the flowchart illustrated in FIG. 14.

First, in Step S1, in a state where the ultrasound probe 21 is brought into contact with a body surface of the subject by the user in order to capture the minor axis image of the blood vessel B of the subject, the B-mode image UB is generated, and the generated B-mode image UB is displayed on the display device 9. In the generation of the B-mode image UB, ultrasound beams are transmitted from the plurality of transducers of the transducer array 2 in accordance with the drive signals from the transmission circuit 3. A reception signal is output to the reception circuit 4 from each transducer which has received the ultrasound echo from the subject. The reception signals are amplified by the amplification unit 23 and subjected to AD conversion by the AD conversion unit 24 and then, are phased and added by the beam former 25 to generate the reception data. The B-mode image signal is obtained by performing the envelope detection processing on the reception data by the signal processing unit 26 in the B-mode processing unit 6. The B-mode image signal is output to the display control unit 8 via the DSC 27 and the image processing unit 28, and the B-mode image UB is displayed on the display device 9 under control of the display control unit 8.

In Step S2, the first vascular wall detection unit 10 sets the search region R1 in the B-mode image UB generated in Step S1 and determines whether or not the minor axis image of the blood vessel B is present in the set search region R1. In this case, for example, as illustrated in FIG. 4, the first vascular wall detection unit 10 creates the brightness profile as illustrated in FIG. 5 by detecting the brightness of the image on the search line SL1 while scanning the virtual search line SL1 extending along the depth direction D1 in the lateral direction D2 in the search region R1.

The first vascular wall detection unit 10 calculates the difference L1 between the two depths J1 and J2 at which brightness value is the maximal value greater than the constant brightness threshold value K1 in the brightness profile created while the search line SL1 is scanned in the lateral direction D2. For example, in a case where the value of the difference L1 calculated while the search line SL1 is scanned from one end to the other end of the search region R1 in the lateral direction D2 changes to have the maximal value, the first vascular wall detection unit 10 determines that the minor axis image of the blood vessel B is present in the search region R1. In addition, in a case where the value of the difference L1 does not change to have the maximal value and is almost constant, the first vascular wall detection unit 10 determines that the minor axis image of the blood vessel B is not present in the search region R1.

In Step S2, in a case where it is determined that the minor axis image of the blood vessel B is not present in the search region R1, a return is made to Step S1, and the B-mode image UB is generated while a position and a direction of the ultrasound probe 21 are adjusted by the user.

In Step S2, in a case where it is determined that the minor axis image of the blood vessel B is present in the search region R1, the first vascular wall detection unit 10 detects the trajectories of the points X1 and X2 corresponding to the depths J1 and J2 at which the brightness value is the maximum in the brightness profile as the vascular wall. In addition, the first vascular wall detection unit 10 transmits the information of the positions of the points X1M and X2M corresponding to the depths J1M and J2M at which the difference L1 calculated while the search line SL1 is scanned in the lateral direction D2 is the maximum value L1M, to the first blood vessel diameter calculation unit 11.

In Step S3, the first blood vessel diameter calculation unit 11 calculates the first blood vessel diameter DF corresponding to the diameter of the blood vessel B by measuring a distance between the points X1M and X2M on the vascular wall that are detected in Step S2 and correspond to the depths J1M and J2M at which the difference L1 is the maximum. As illustrated in FIG. 4, the first blood vessel diameter calculation unit 11 displays the calculated first blood vessel diameter DF on the display device 9.

In subsequent Step S4, in order to capture the major axis image of the blood vessel B, the direction of the ultrasound probe 21 is changed by the user, and the B-mode image UB is generated.

In Step S5, the second vascular wall detection unit 12 determines whether or not the major axis image of the blood vessel B is present in the B-mode image UB generated in Step S4. In this case, for example, as illustrated in FIG. 6, the second vascular wall detection unit 12 sets the search region R2 on the B-mode image UB and detects the brightness on the search line SL2 while scanning the virtual search line SL2 extending along the depth direction D1 in the lateral direction D2 in the set search region R2. Accordingly, the second vascular wall detection unit 12 creates the brightness profile as illustrated in FIG. 7.

The second vascular wall detection unit 12 calculates the difference L2 between the two depths J3 and J4 at which the brightness value is the maximal value greater than the constant brightness threshold value K2 in the brightness profile created while the search line SL2 is scanned in the lateral direction D2. In a case where the value of the calculated difference L2 is almost constant, the second vascular wall detection unit 12 determines that the major axis image of the blood vessel B is present in the search region R2 of the B-mode image UB. In a case where the value of the difference L2 does not have an almost constant value, the second vascular wall detection unit 12 determines that the major axis image of the blood vessel B is not present in the search region R2.

In Step S5, in a case where it is determined that the major axis image of the blood vessel B is not present in the B-mode image UB, a return is made to Step S4. The position and the direction of the ultrasound probe 21 are adjusted by the user, and the B-mode image UB is newly generated.

In Step S5, in a case where it is determined that the major axis image of the blood vessel B is present in the B-mode image UB, the second vascular wall detection unit 12 detects positions of the depths J3 and J4 at which the brightness value is the maximal value in the recognized major axis image of the blood vessel B, as the position of the anterior vascular wall W1 and the position of the posterior vascular wall W2, respectively.

In Step S6, the second blood vessel diameter calculation unit 13 calculates the second blood vessel diameter DS corresponding to the diameter of the blood vessel B based on the major axis image of the blood vessel B detected in Step S5. For example, the second blood vessel diameter calculation unit 13 calculates the maximum distance among the distances between the anterior vascular wall W1 and the posterior vascular wall W2 in the depth direction D1 as the second blood vessel diameter DS. As illustrated in FIG. 6, the second blood vessel diameter calculation unit 13 displays the calculated second blood vessel diameter DS on the display device 9.

In Step S7, the second blood vessel diameter calculation unit 13 determines whether or not the second blood vessel diameter DS has a value within the determined range including the first blood vessel diameter DF by comparing the calculated second blood vessel diameter DS with the first blood vessel diameter DF calculated in Step S3. For example, the determined range is set as a range that has a lower limit value lower than the first blood vessel diameter DF by a constant value and has an upper limit value higher than the first blood vessel diameter DF by a constant value.

In Step S7, in a case where it is determined that the second blood vessel diameter DS is outside the determined range, a return is made to Step S4, and the processing of Step S4 to Step S7 is performed again. In this case, the user adjusts the position of the ultrasound probe 21 to approximate the value of the second blood vessel diameter DS to a value of the first blood vessel diameter DF while checking the value of the second blood vessel diameter DS displayed on the display device 9.

In Step S7, in a case where it is determined that the second blood vessel diameter DS is within the determined range, it is determined that the B-mode image UB including the major axis image of the blood vessel B having the first blood vessel diameter DF, that is, the major axis image of the blood vessel B representing the longitudinal cross section passing through the center of the blood vessel B, is obtained, and a transition is made to Step S8.

In Step S8, the second vascular wall detection unit 12 estimates the gradient of the blood vessel B using the B-mode image UB that is obtained in Step S7 and includes the major axis image of the blood vessel B having the second blood vessel diameter DS within the determined range, and estimates the blood vessel traveling angle BA from the estimated gradient of the blood vessel B. For example, the second vascular wall detection unit 12 can estimate the gradient of the blood vessel B by estimating the straight line passing through the plurality of positions on the anterior vascular wall W1 and the straight line passing through the plurality of positions on the posterior vascular wall W2 detected in Step S5 and averaging the inclinations of the estimated two straight lines, and can obtain the virtual blood vessel gradient line BL representing the gradient of the blood vessel B as illustrated in FIG. 8. The second vascular wall detection unit 12 can estimate the angle between the obtained blood vessel gradient line BL and the virtual straight line AL along the depth direction D1 of the B-mode image UB as the blood vessel traveling angle BA.

In subsequent Step S9, the second vascular wall detection unit 12 sets the B-mode steer angle representing the inclination angle of the scan line in the generation of the B-mode image UB by the B-mode processing unit 6, using the blood vessel traveling angle BA estimated in Step S8. In this case, for example, the second vascular wall detection unit 12, using the blood vessel traveling angle BA, the determined angle A1 illustrated in FIG. 9, and the determined angle A2 greater than the angle A1, can set the B-mode steer angle to 0 degrees in a case where a relationship of 90−BA<A1/2 is satisfied, set the B-mode steer angle to the angle A1 in a case where a relationship of A1/2≤90−BA<A2/2 is satisfied, and set the B-mode steer angle to the angle A2 in a case where a relationship of A2/2≤90−BA is satisfied. Here, for example, the angle A1 can be set to 7.5 degrees in advance, and the angle A2 can be set to 15 degrees in advance.

In Step S10, the second vascular wall detection unit 12 sets the Doppler steer angle representing the inclination angle of the scan line in the acquisition of the Doppler data by the Doppler processing unit 7, using the blood vessel traveling angle BA estimated in Step S8. In this case, for example, the second vascular wall detection unit 12, using the blood vessel traveling angle BA, the determined angle B1, and the angle B2 greater than the angle B1 as illustrated in FIG. 10, can set the Doppler steer angle to 0 degrees in a case where a relationship of BA<60 is satisfied, set the Doppler steer angle to the angle B1 in a case where a relationship of 60≤BA<60+B1 is satisfied, and set the Doppler steer angle to the angle B2 in a case where a relationship of 60+B1≤BA is satisfied. Here, for example, the angle B1 can be set to 15 degrees in advance, and the angle B2 can be set to 30 degrees in advance.

In Step S11, as illustrated in FIG. 12, the gate setting unit 14 sets the Doppler gate DG having the center position and the size decided based on the coordinates of the anterior vascular wall W1 and the coordinates of the posterior vascular wall W2 detected in Step S5, in the blood vessel region BR on the B-mode image UB used for estimating the blood vessel traveling angle BA in Step S8. In this case, the gate setting unit 14 can set, as the center position of the Doppler gate DG, the midpoint C between the positions of the two points X3 and X4 detected as the position of the anterior vascular wall W1 and the position of the posterior vascular wall W2 in Step S5, and set the length calculated by multiplying the second blood vessel diameter DS measured in Step S6 by the determined value as the gate width LG of the Doppler gate DG. Here, the determined value by which the second blood vessel diameter DS is multiplied is a number such as 0.75 that is greater than 0 and less than or equal to 1.00, and for example, may be decided by the input operation of the user through the input device 18.

In addition, as illustrated in FIG. 12, the gate setting unit 14 displays the set Doppler gate DG on the display device 9 in a superimposed manner on the B-mode image UB.

Figure 17:
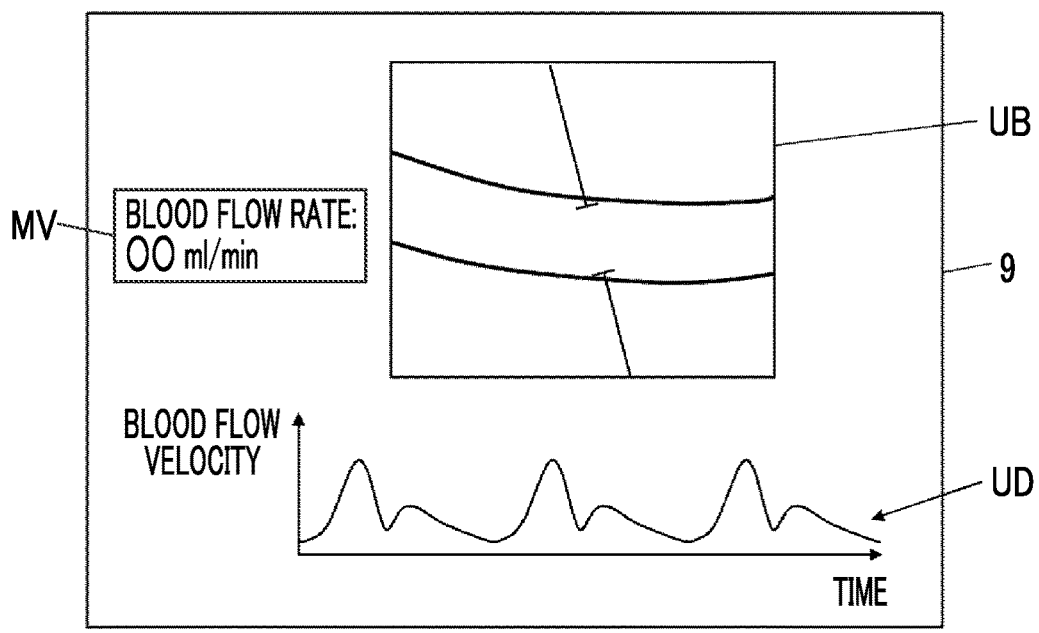
FIG. 17 is a diagram schematically illustrating the B-mode image, the Doppler waveform image, and a measurement value of the blood flow rate displayed on the display device in the first embodiment of the present invention.

In Step S12, the Doppler processing unit 7 starts continuously generating the Doppler waveform image, and displays the generated Doppler waveform image on the display device 9. In this case, the Doppler processing unit 7 acquires the Doppler data in the Doppler gate DG set in Step S10 as illustrated in FIG. 12, continuously generates the Doppler waveform image based on the acquired Doppler data, and displays the generated Doppler waveform image on the display device 9. In addition, the B-mode processing unit 6 also starts continuously generating the B-mode image UB and displays the generated B-mode image UB on the display device 9. Accordingly, both of the B-mode image UB and the Doppler waveform image are continuously generated, and the B-mode image UB and a Doppler waveform image UD are displayed on the display device 9 as illustrated in FIG. 17.

Figure 15:
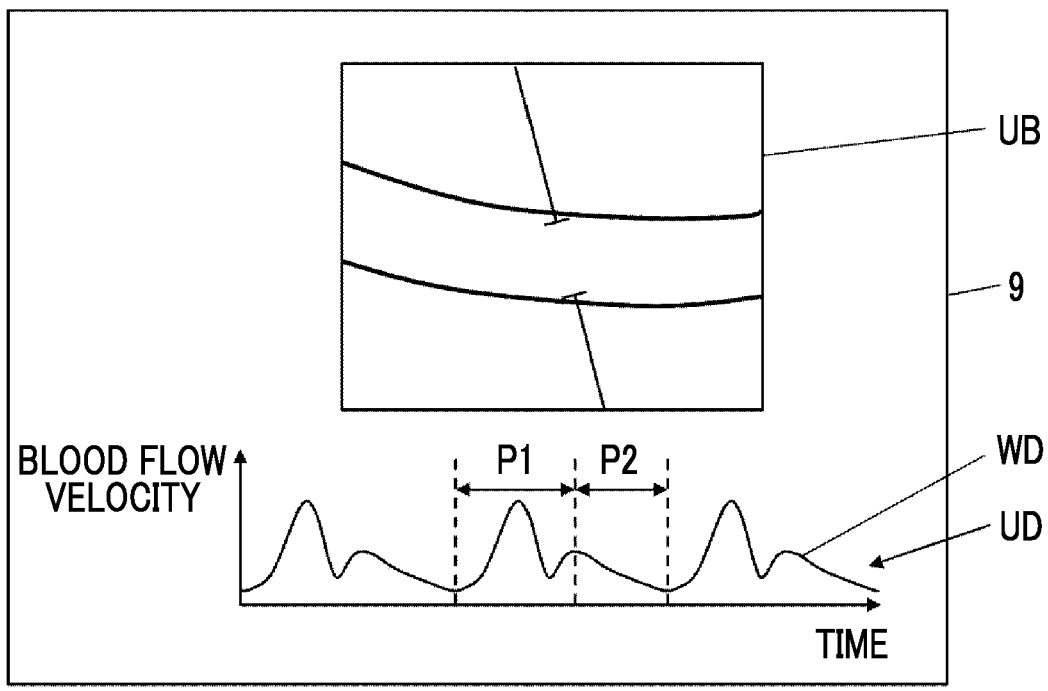
FIG. 15 is a diagram schematically illustrating the B-mode image and a Doppler waveform image displayed on the display device in the first embodiment of the present invention.

In Step S13, a Doppler waveform WD in the Doppler waveform image UD generated in Step S11 is adjusted such that the Doppler data is accurately acquired by the Doppler processing unit 7. In general, as illustrated in FIG. 15, the Doppler waveform WD periodically changes in accordance with a heartbeat. Thus, for example, the Doppler waveform WD is adjusted from a time point at which a start position and an end position of a heartbeat cycle are detected. In addition, the adjustment of the Doppler waveform WD includes adjustment of a horizontal axis, that is, a baseline position, of a graph of the Doppler waveform WD, and adjustment of a scale on a vertical axis of the Doppler waveform WD. In the adjustment of the Doppler waveform WD, not only display of the Doppler waveform WD in the display device 9 is adjusted, but also a repetition frequency of ultrasound pulses transmitted into the subject from the transducer array 2 of the ultrasound probe 21 is adjusted by controlling the transmission circuit 3 by the device control unit 17. In this manner, for example, the Doppler waveform WD is adjusted such that the maximum value and the minimum value of the Doppler waveform WD fall within 70% of the scale on the vertical axis.

In general, the blood flow velocity in the blood vessel is increased during systole of a heart and is decreased during diastole of a heart. Thus, as illustrated in FIG. 15, an amount of change of the Doppler waveform WD is large in systole P1, and the amount of change of the Doppler waveform WD is small in diastole P2. Therefore, in Step S14, cycle information of the Doppler waveform WD is acquired, and whether or not the current time point is in the diastole P2 of the heart of the subject is determined based on the acquired cycle information. In a case where it is determined that the current time point is not in the diastole P2 of the heart of the subject, the processing of Step S14 is performed again. In a case where it is determined that the current time point is in the diastole P2 of the heart of the subject, a transition is made to Step S15.

In Step S15, the display of both of the B-mode image UB and the Doppler waveform image UD displayed on the display device 9 is frozen. Here, freezing the display of the B-mode image UB and the Doppler waveform image UD means that in a state where the B-mode image UB continuously generated by the B-mode processing unit 6 and the Doppler waveform image UD continuously generated by the Doppler processing unit 7 are displayed on the display device 9, the display of the B-mode image UB and the Doppler waveform image UD is temporarily stopped, and one still B-mode image UB and one still Doppler waveform image UD are displayed on the display device 9.

In this manner, the Doppler data in the diastole P2 in which the amount of change of the Doppler waveform WD is small can be used for measuring the blood flow rate.

Figure 16:
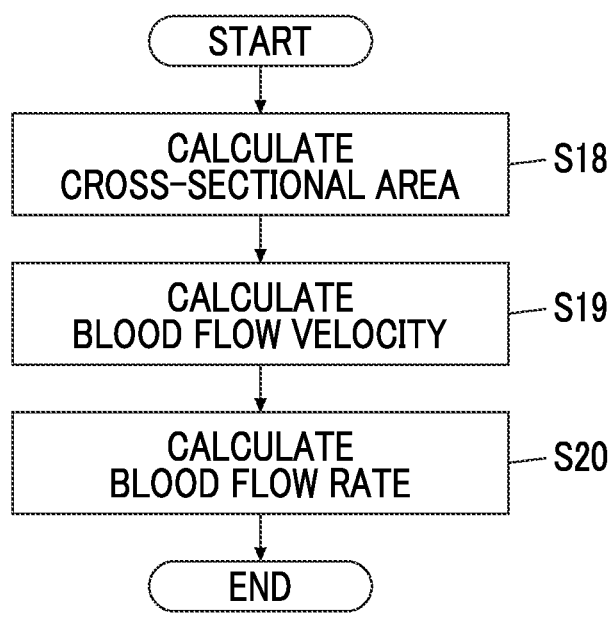
FIG. 16 is a flowchart illustrating an operation of automatically measuring a blood flow rate in the first embodiment of the present invention.

In subsequent Step S16, the blood flow rate in the blood vessel region BR is automatically measured. Step S16 will be described using the flowchart illustrated in FIG. 16. Step S16 is configured with Step S18 to Step S20.

First, in Step S18, assuming that the blood vessel B has a circular cross section, the blood flow rate measurement unit 16 calculates the cross-sectional area of the blood vessel B based on the second blood vessel diameter DS that is determined as being within the determined range in Step S7.

Next, in Step S19, the blood flow velocity calculation unit 15 calculates the blood flow velocity based on the Doppler data acquired by the Doppler processing unit 7 when the display of the B-mode image UB and the Doppler waveform image UD is frozen in Step S15. In this case, the blood flow velocity calculation unit 15 can calculate the average blood flow velocity in the heartbeat periods.

In subsequent Step S20, the blood flow rate measurement unit 16 calculates the blood flow rate representing the volume of the blood flowing in the blood vessel B per unit time based on the cross-sectional area of the blood vessel B calculated in Step S18 and the blood flow velocity calculated in Step S19.

In this manner, the automatic measurement of the blood flow rate in Step S16 is completed.

In Step S17, a measurement result of the blood flow rate obtained in Step S16 is displayed on the display device 9. For example, as illustrated in FIG. 17, a measurement value MV of the blood flow rate is displayed on the display device 9 together with the B-mode image UB and the Doppler waveform image UD.

In this manner, in a case where the measurement value MV of the blood flow rate is displayed on the display device 9, the operation of the ultrasound diagnostic apparatus 1 is ended.

As described above, according to the ultrasound diagnostic apparatus 1 according to the first embodiment of the present invention, the first blood vessel diameter DF is calculated based on the B-mode image UB representing the minor axis image of the blood vessel B. The B-mode image UB representing the major axis image passing through the center of the blood vessel B is accurately acquired based on the first blood vessel diameter DF. The blood flow rate is measured using the acquired B-mode image UB representing the major axis image of the blood vessel B. Thus, fluctuation of measurement accuracy of the blood flow rate caused by adjusting the position of the ultrasound probe 21 on the body surface of the subject by the user can be reduced, and the measurement accuracy can be improved.

In addition, by acquiring the B-mode image UB representing the major axis image passing through the center of the blood vessel B, the blood flow rate is automatically measured, and the measurement result of the blood flow rate is displayed on the display device 9. Thus, the blood flow rate can be easily measured.

Particularly, while illustration is not provided, for example, even in a case where both hands of the user are not empty, such as in a case where the display device 9 is configured with a small portable display and the user holds the display device 9 in one hand and the ultrasound probe 21 in the other hand, the user does not need to perform an operation through the input device 18 or the like according to the ultrasound diagnostic apparatus 1 according to the first embodiment of the present invention. Thus, the blood flow rate can be easily measured.

In Step S2, while the first vascular wall detection unit 10 sets the search region R1 on the B-mode image UB and searches for the minor axis image of the blood vessel B in the set search region R1, the minor axis image of the blood vessel B can also be searched for over the entire B-mode image UB. However, considering a point of quickly recognizing the minor axis image of the blood vessel B by reducing a calculation amount required for processing the search for the blood vessel B, it is preferable to search for the minor axis image of the blood vessel B in the search region R1.

Similarly, even in Step S5, while the major axis image of the blood vessel B may be searched for over the B-mode image UB, it is preferable to search for the major axis image of the blood vessel B in the search region R2 from a point of quickly recognizing the major axis image of the blood vessel B.

In addition, in a case where the minor axis image of the blood vessel B is captured, a position of the minor axis image of the blood vessel B in the lateral direction D2 is likely to change on the continuously generated B-mode image UB of a plurality of frames because of a slight change in inclination, a change in position, and the like of the ultrasound probe 21 in contact with the body surface of the subject. Thus, for example, the first vascular wall detection unit 10 tracks and recognizes the minor axis image of the blood vessel B by detecting movement of the minor axis image of the blood vessel B between continuous frames of the B-mode image UB. For example, the detection of the movement of the minor axis image of the blood vessel B can use a method of general image analysis such as so-called pattern matching in addition to a method of comparing the brightness profile obtained by scanning the search line SL1 over the B-mode image UB with the brightness profile with respect to the already detected minor axis image of the blood vessel B.

In this manner, by tracking the minor axis image of the blood vessel B, the first blood vessel diameter DF of the minor axis image of the blood vessel B can be easily calculated even in a case where the minor axis image of the blood vessel B moves between continuous frames.

Figure 18:
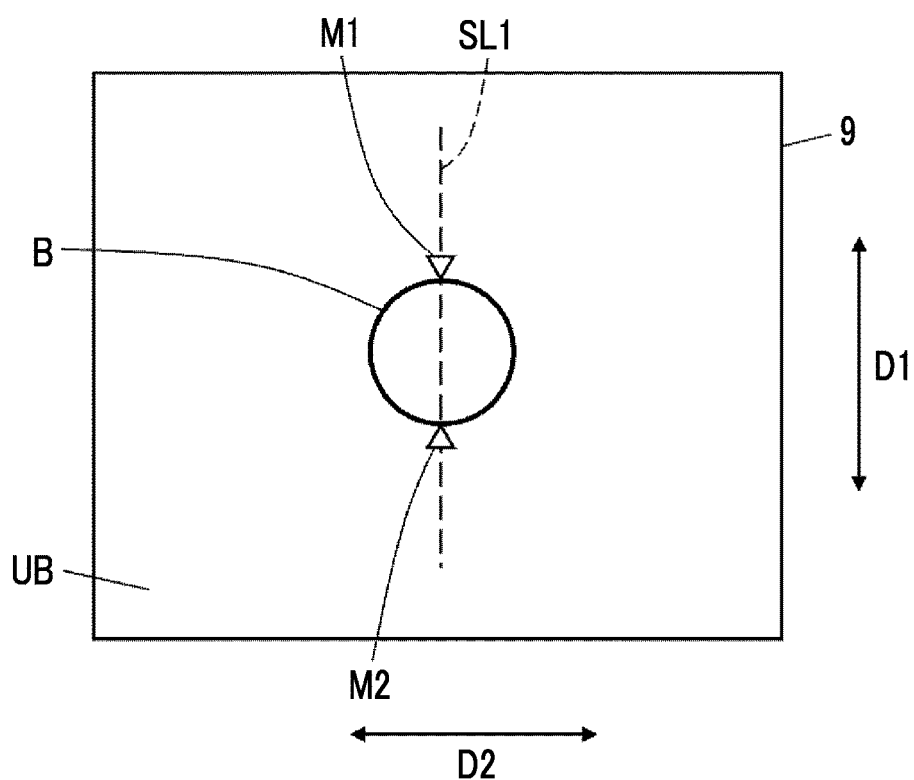
FIG. 18 is a diagram schematically illustrating a measurement point marker arranged with respect to the minor axis image of the blood vessel.

In addition, for example, in Step S2, in a case where the minor axis image of the blood vessel B is recognized, measurement point markers M1 and M2 may be displayed at positions of two intersections between the search line SL1 passing through the center of the blood vessel B and the contours of the blood vessel B, that is, positions of the depths J1 and J2 at which the difference L1 in the depth direction D1 between the depths J1 and J2 measured in Step S2 is the maximum, on the display device 9 as illustrated in FIG. 18. In this manner, by displaying the measurement point markers M1 and M2, the user can perceive the recognition of the minor axis image of the blood vessel B in Step S2 and a measurement position of the blood vessel diameter.

Figure 19:
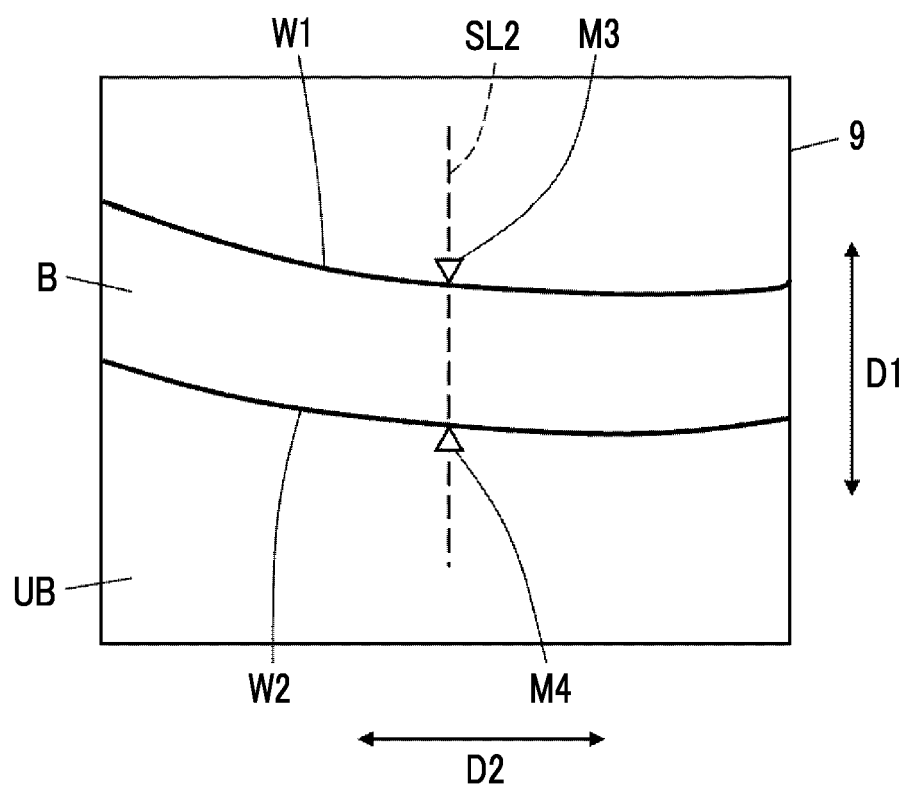
FIG. 19 is a diagram schematically illustrating a measurement point marker arranged with respect to the major axis image of the blood vessel.

In addition, similarly, in Step S5, in a case where the major axis image of the blood vessel B is recognized, measurement point markers M3 and M4 can be displayed at a position of an intersection between the search line SL2 and the anterior vascular wall W1 and a position of an intersection between the search line SL2 and the posterior vascular wall W2 on the display device 9 as illustrated in FIG. 19.

In addition, in a case where the minor axis image of the blood vessel B is recognized, a display aspect such as a color, a thickness, and the like of contours of the recognized minor axis image of the blood vessel B may be changed instead of displaying the measurement point markers M1 and M2. Similarly, in a case where the major axis image of the blood vessel B is recognized, a display aspect such as a color, a thickness, and the like of contours of the recognized major axis image of the blood vessel B can be changed instead of displaying the measurement point markers M3 and M4.

In addition, in Step S2 and Step S5, while the brightness profiles of the image along the search lines SL1 and SL2 are used for recognizing the minor axis image and the major axis image of the blood vessel B, a method of recognizing the minor axis image and the major axis image of the blood vessel B is not limited thereto. For example, a method of so-called template matching by storing typical pattern data of the minor axis image and the major axis image of the blood vessel B in advance as templates, calculating a similarity with respect to the pattern data while searching in the B-mode image UB using the templates, and determining that the minor axis image or the major axis image of the blood vessel B is present in a location in which the similarity is greater than or equal to a threshold value and is the maximum may be used.

In addition, the calculation of the similarity can use, in addition to simple template matching, for example, a machine learning method disclosed in Csurka et al.: Visual Categorization with Bags of Keypoints, Proc. of ECCV Workshop on Statistical Learning in Computer Vision, pp. 59-74 (2004) or a general image recognition method using deep learning disclosed in Krizhevsk et al.: ImageNet Classification with Deep Convolutional Neural Networks, Advances in Neural Information Processing Systems 25, pp. 1106-1114 (2012).

In addition, in Step S3, while the first blood vessel diameter DF is calculated based on information of the vascular wall detected in Step S2 with respect to the B-mode image UB of one frame, the first blood vessel diameter DF may be calculated based on the information of the vascular wall detected with respect to the B-mode image UB of a plurality of frames. For example, in a case where the value of the first blood vessel diameter DF calculated over a determined number of frames such as 5 to 10 frames is less than or equal to a constant value, the first blood vessel diameter calculation unit 11 can calculate the maximum first blood vessel diameter DF among the first blood vessel diameters DF calculated with respect to the B-mode image UB of the determined number of frames as the final value of the first blood vessel diameter DF. In addition, for example, the first blood vessel diameter calculation unit 11 can calculate an average value of the first blood vessel diameters DF calculated with respect to the B-mode image UB of the determined number of frames as the final value of the first blood vessel diameter DF.

Accordingly, since a case where the calculated first blood vessel diameter DF has an abnormal value such as a significantly large value or a significantly small value with respect to the actual diameter of the blood vessel B can be excluded, the final value of the first blood vessel diameter DF can be accurately calculated.

In addition, the determination of Step S7 can be performed based on the second blood vessel diameter DS calculated with respect to the B-mode image UB of a plurality of frames. For example, in a case where the second blood vessel diameter DS calculated over a determined number of frames such as 5 to 10 frames maintains a determined range such as 5 to 10 frames including the first blood vessel diameter DF calculated in Step S3, the second blood vessel diameter calculation unit 13 can determine that the second blood vessel diameter DS has a value within the determined range, and a transition can be made to Step S8. Accordingly, accuracy of the determination of Step S7 can be improved, and the B-mode image UB representing the longitudinal cross section passing through the center of the blood vessel B can be accurately acquired.

In addition, the second blood vessel diameter calculation unit 13 can calculate the value of the maximum second blood vessel diameter DS among the second blood vessel diameters DS calculated with respect to the B-mode image UB of the determined number of frames used in the determination of the second blood vessel diameter DS as having a value within the determined range, as the final value of the second blood vessel diameter DS. In this case, for example, the second vascular wall detection unit 12 can perform the processing of Step S8 to Step S11 using the B-mode image UB used for calculating the final second blood vessel diameter DS.

In addition, the second blood vessel diameter calculation unit 13 can average the second blood vessel diameters DS calculated with respect to the B-mode image UB of the determined number of frames used in the determination of the second blood vessel diameter DS as having a value within the determined range, and calculate a calculated average value as the final value of the second blood vessel diameter DS. In this case, for example, the second vascular wall detection unit 12 can perform the processing of Step S8 to Step S11 using the B-mode image UB that is lastly acquired among the determined number of frames of the B-mode image UB.

In addition, the value of the first blood vessel diameter DF calculated in Step S3 can be displayed together with the major axis image of the blood vessel B and the value of the second blood vessel diameter DS displayed on the display device 9 in Step S5 to Step S7. In this case, the user can adjust the position of the ultrasound probe 21 to approximate the second blood vessel diameter DS calculated in Step S6 to the first blood vessel diameter DF while checking the value of the first blood vessel diameter DF. Thus, the user can more easily adjust the position of the ultrasound probe 21.

In addition, in the calculation of the first blood vessel diameter DF in Step S3, for example, the first blood vessel diameter calculation unit 11 can calculate a distance between the minor axis image of the blood vessel B and the body surface of the subject as a first blood vessel depth based on the relatively shallow depth J1 out of the depths J1 and J2 corresponding to the positions of the vascular wall detected in Step S2, and display the calculated first blood vessel depth on the display device 9.

In addition, in the calculation of the second blood vessel diameter DS in Step S6, for example, the second blood vessel diameter calculation unit 13 can calculate a distance between the anterior vascular wall W1 and the body surface of the subject as a second blood vessel depth based on the depth J3 corresponding to the position of the anterior vascular wall W1 detected in Step S5, and display the calculated second blood vessel depth on the display device 9.

Here, in Step S4 to Step S7, both of the calculated first blood vessel depth and the second blood vessel depth can be displayed on the display device 9. Accordingly, by comparing the first blood vessel depth with the second blood vessel depth, the user can adjust the position of the ultrasound probe 21 while checking whether or not the major axis image of the blood vessel B in the B-mode image UB generated in Step S4 corresponds to the minor axis image of the blood vessel B in the B-mode image UB generated in Step S1. Accordingly, the major axis image of the blood vessel B not corresponding to the minor axis image of the blood vessel B in the B-mode image UB generated in Step S1 is prevented from being captured in Step S4, and an appropriate major axis image of the blood vessel B can be captured. Thus, the measurement accuracy of the blood flow rate can be improved.

In addition, for example, the first blood vessel depth may be considered in the recognition of the major axis image of the blood vessel B in Step S5. For example, in a case where the width of change of the difference L2 between the depths J3 and J4 calculated while the search line SL2 is scanned in the lateral direction D2 is less than or equal to a width of change threshold value, and furthermore, the second blood vessel depth has a value within a depth range including the first blood vessel depth, the second vascular wall detection unit 12 determines that the major axis image of the blood vessel B is present in the search region R2. In addition, in a case where the width of change of the difference L2 calculated while the search line SL2 is scanned in the lateral direction D2 is greater than the width of change threshold value, or the second blood vessel depth has a value outside the depth range, it is determined that the major axis image of the blood vessel B is not present in the search region R2.

Accordingly, the major axis image of the blood vessel B not corresponding to the minor axis image of the blood vessel B in the B-mode image UB generated in Step S1 can be prevented from being captured in Step S4.

In addition, by providing a step of continuously generating the B-mode image UB including the major axis image of the blood vessel B and determining that the position of the major axis image of the blood vessel B is stable between Step S11 and Step S12, a transition can be made to Step S11 based on a trigger that the position of the major axis image of the blood vessel B is stable. For example, in the B-mode image UB of the plurality of frames generated within a determined time such as one second, for example, in a case where a change in position of the major axis image of the blood vessel B is less than or equal to a determined value such as 0.2 mm, it is determined that the position of the major axis image of the blood vessel B is stable. In addition, in the B-mode image UB of the plurality of frames generated within a determined time such as one second, for example, in a case where the change in position of the major axis image of the blood vessel B is greater than a determined value such as 0.2 mm, it is determined that the position of the major axis image of the blood vessel B is not stable.

In this manner, since the processing from Step S11 is performed based on a trigger that the position of the major axis image of the blood vessel B in the B-mode image UB is stable, that is, the position of the ultrasound probe 21 arranged on the body surface of the subject is stable, the blood flow rate can be measured using a stable image, and the measurement accuracy of the blood flow rate can be improved.

In addition, while the processing of Step S5 to Step S7 is performed with respect to the B-mode image UB generated in Step S4, the processing of Step S5 to Step S7 can be performed with respect to the B-mode image UB generated in any of Step S12 to Step S14. In this case, for example, the calculation of the cross-sectional area of the blood vessel B in Step S18 may be performed using the second blood vessel diameter DS that is calculated with respect to the B-mode image UB generated in any of Step S12 to Step S14 and is determined as being within the determined range including the first blood vessel diameter DF calculated in Step S3, instead of the second blood vessel diameter DS determined as being within the determined range in Step S7.

In addition, in Step S18, the blood flow rate measurement unit 16 may calculate the cross-sectional area of the blood vessel B based on the first blood vessel diameter DF calculated in Step S3 instead of calculating the cross-sectional area of the blood vessel B based on the second blood vessel diameter DS determined as being within the determined range. For example, in a case where the first blood vessel diameter DF is greater than the second blood vessel diameter DS determined as being within the determined range, the cross-sectional area of the blood vessel B is calculated based on the first blood vessel diameter DF.

In addition, while the Doppler waveform image UD is generated in Step S12, and the generated Doppler waveform image UD is displayed on the display device 9, the Doppler waveform image UD may not necessarily be displayed on the display device 9 as long as data of the Doppler waveform WD is acquired. In this manner, even in a case where the Doppler waveform image UD is not displayed on the display device 9, the blood flow rate is measured in Step S16 based on the data of the Doppler waveform WD acquired in Step S13 and the second blood vessel diameter DS determined as being within the determined range in Step S7, in the same manner as in a case where the Doppler waveform image UD is displayed on the display device 9. In addition, in a case where the Doppler waveform image UD is not displayed on the display device 9, the acquisition of the data of the Doppler waveform WD may be simply stopped instead of freezing the display of the Doppler waveform image UD on the display device 9 in Step S15.

In addition, in Step S13, while an example in which the Doppler waveform WD is adjusted from the time point at which the start position and the end position of the heartbeat cycle in the Doppler waveform WD are detected is illustrated, for example, the adjustment of the Doppler waveform WD in Step S13 may be automatically performed based on a trigger that a constant time such as two seconds has elapsed from a time point at which the generation of the Doppler waveform image UD is started in Step S12.

In addition, in the adjustment of the Doppler waveform WD, a position of the Doppler gate DG may be adjusted again such that the maximum value and the minimum value of the Doppler waveform WD fall within 70% of the scale on the vertical axis, in addition to the adjustment of the baseline position and the adjustment of the scale on the vertical axis of the Doppler waveform WD.

In addition, for example, Step S13 can be omitted. However, adjusting the Doppler waveform WD can improve accuracy of the blood flow velocity calculated by the blood flow velocity calculation unit 15 and improve accuracy of the blood flow rate measured by the blood flow rate measurement unit 16. Thus, it is preferable to perform Step S12.

In addition, in Step S14, while a transition is made to next Step S15 based on a trigger that the current time point is in the diastole P2 of the heart of the subject, the trigger for a transition from Step S14 to Step S15 is not limited thereto.

For example, whether or not the current time point is in the systole P1 may be determined instead of determining whether or not the current time point is in the diastole P2. In this case, in a case where it is determined that the current time point is not in the systole P1, whether or not the current time point is in the systole P1 is determined again. In a case where it is determined that the current time point is in the systole P1, a transition is made to subsequent Step S15. However, since the amount of change of the Doppler waveform WD is smaller in the diastole P2 than in the systole P1, it is more preferable to transition to Step S15 based on a trigger that the current time point is in the diastole P2 than to transition to Step S15 based on a trigger that the current time point is in the systole P1.

In addition, for example, instead of performing Step S14, a transition can be made to Step S15 based on a trigger that a constant time such as two seconds has elapsed from a time point at which an operation of adjusting the Doppler waveform WD in Step S13 is completed.

In addition, for example, instead of performing Step S14, a transition can be made to Step S15 based on a trigger of a time point at which start positions and end positions of a plurality of heartbeat cycles such as two cycles or three cycles are detected in the Doppler waveform WD.

In addition, in the freezing of the display of the B-mode image UB and the Doppler waveform image UD on the display device 9 in Step S15, for example, the Doppler waveform image UD may be displayed by scrolling back to match an end position of the diastole P2 or an end position of the systole P1 in the Doppler waveform WD to a right end portion of the Doppler waveform image UD. In this manner, by changing a position of the Doppler waveform WD displayed on the display device 9 after the display of the B-mode image UB and the Doppler waveform image UD is frozen, a time phase of the B-mode image UB displayed on the display device 9 can be matched to the diastole P2 or the systole P1.

In addition, while the estimation of the blood vessel traveling angle BA in Step S8 is performed after it is determined that the second blood vessel diameter DS has a value within the determined range in Step S7, the processing of Step S8 may be performed among Step S5 to Step S7. A timing of the estimation of the blood vessel traveling angle BA is not particularly limited as long as the estimation of the blood vessel traveling angle BA is performed before the processing of Step S9 to Step S11.

In addition, in Step S6, while the second blood vessel diameter calculation unit 13 calculates the distance in the depth direction D1 between the anterior vascular wall W1 and the posterior vascular wall W2 detected in Step S5 as the second blood vessel diameter DS, for example, a blood vessel diameter in a direction orthogonal to the traveling direction of the blood vessel B can be calculated as the second blood vessel diameter DS by performing the processing of estimating the blood vessel traveling angle BA in Step S8 before the processing of calculating the second blood vessel diameter DS in Step S6 to set the search line SL2 again to a direction orthogonal to the blood vessel gradient line BL illustrated in FIG. 6. Accordingly, the measurement accuracy of the blood flow rate can be improved by more accurately calculating the second blood vessel diameter DS.

In addition, in Step S8, while the second vascular wall detection unit 12 estimates the gradient of the blood vessel based on both of the anterior vascular wall W1 and the posterior vascular wall W2, the virtual blood vessel gradient line BL representing the gradient of the blood vessel can be estimated based on any one of the anterior vascular wall W1 or the posterior vascular wall W2.

In addition, while the Doppler steer angle is set in Step S10 after the B-mode steer angle is set in Step S9, and the Doppler gate DG is set in Step S11 after the Doppler steer angle is set, an order in which Step S9 to Step S11 are performed is not particularly limited and can be rearranged. For example, after the B-mode steer angle is set in Step S9, the setting of the Doppler steer angle in Step S10 and the setting of the Doppler gate DG in Step S11 can be performed in parallel. In addition, for example, the processing of Step S9 to Step S11 can be performed in an order of the setting of the Doppler steer angle in Step S10, the setting of the Doppler gate DG in Step S11, and the setting of the B-mode steer angle in Step S9.

In addition, in Step S10, while the second vascular wall detection unit 12 sets the Doppler steer angle such that the angle correction value for the blood vessel traveling angle BA is within 60 degrees, the blood vessel traveling angle BA can be set as the angle correction value of the Doppler steer angle. In this case, the angle correction value of the Doppler steer angle may exceed 60 degrees. However, when the angle correction value of the Doppler steer angle exceeds 60 degrees, information representing that the angle correction value exceeds 60 degrees can be displayed on the display device 9. For example, the user can check the information representing that the angle correction value exceeds 60 degrees, and perform the automatic measurement of the blood flow velocity by the ultrasound diagnostic apparatus 1 again by adjusting the inclination or the like of the ultrasound probe 21 in contact with the subject.

In addition, after the Doppler gate DG is set in Step S11, the blood vessel region BR including the Doppler gate DG can be displayed on the display device 9 by enlarging the blood vessel region BR in the B-mode image UB. Thus, the blood vessel region BR on the enlarged B-mode image UB can be clearly checked. In addition, in this case, the blood vessel diameter is measured based on the enlarged B-mode image UB. For example, detecting the vascular wall based on the B-mode image UB after the enlargement can detect the position of the vascular wall more accurately than detecting the vascular wall based on the B-mode image UB before the enlargement because of a resolution of the B-mode image UB. Thus, the measurement accuracy of the blood flow rate can be improved by measuring the blood vessel diameter based on the enlarged B-mode image UB.

In addition, while illustration is not provided, a guide unit that provides guidance to the user can be comprised in the ultrasound diagnostic apparatus 1, and a message for matching the minor axis image of the blood vessel B into the search region R1 can be displayed on the display device 9 by the guide unit in Step S1. Accordingly, the search line SL can be set at a more appropriate position by improving accuracy of recognizing the minor axis image of the blood vessel B by the first vascular wall detection unit 10. Thus, the blood vessel diameter and the cross-sectional area of the blood vessel can be accurately obtained, and the measurement accuracy of the blood flow rate can be improved.

In addition, in this case, similarly, a message for matching the major axis image of the blood vessel B into the search region R2 can be displayed on the display device 9 in Step S4. Accordingly, accuracy of recognizing the major axis image of the blood vessel B by the second vascular wall detection unit 12 can be improved.

In addition, in general, it is known that the blood vessel diameter periodically changes between the minimum diameter and the maximum diameter in accordance with the heartbeat. Therefore, while illustration is not provided, for example, the second blood vessel diameter calculation unit 13 can display a graph illustrating a time change of the second blood vessel diameter DS calculated with respect to the B-mode image UB including the major axis image corresponding to the longitudinal cross section passing through the center of the blood vessel B, that is, the second blood vessel diameter DS corresponding to the diameter of the blood vessel B, on the display device 9 in a superimposed manner on the B-mode image UB. Accordingly, the user can easily perceive the time change of the second blood vessel diameter DS corresponding to the diameter of the blood vessel B.

In addition, by obtaining information of the time change of the second blood vessel diameter DS corresponding to the diameter of the blood vessel B, the minimum diameter and the maximum diameter of the blood vessel B in the major axis image are easily measured. Therefore, for example, an elastic index calculation unit, not illustrated, that measures the minimum diameter and the maximum diameter of the blood vessel B based on the information of the time change of the second blood vessel diameter DS corresponding to the diameter of the blood vessel B and calculates an elastic index representing elasticity of the blood vessel based on the measured minimum diameter and the maximum diameter can be comprised in the ultrasound diagnostic apparatus 1. For example, the elastic index calculation unit can calculate a difference between the minimum diameter and the maximum diameter of the blood vessel as the elastic index. In addition, the elastic index calculation unit can calculate a normalized difference obtained by dividing the difference between the maximum diameter and the minimum diameter of the blood vessel by the minimum diameter of the blood vessel as the elastic index.

In addition, by measuring a blood pressure Q1 of the subject at a time point at which the diameter of the blood vessel is the minimum, and a blood pressure Q2 of the subject at a time point at which the diameter of the blood vessel is the maximum using a blood pressure manometer, not illustrated, the elastic index calculation unit can calculate a stiffness parameter $X=\{Log\ (Q2/Q1)\}/\{(DB/DA)-1\}$ disclosed in JP5384919B as the elastic index using the blood pressures Q1 and Q2, a minimum diameter DA of the blood vessel, and a maximum diameter DB of the blood vessel.

Second Embodiment

While the B-mode image UB and the Doppler waveform image UD are generated in parallel in Step S12 in the operation of the ultrasound diagnostic apparatus 1 of the first embodiment, only the Doppler waveform image UD can be generated by temporarily stopping the generation of the B-mode image UB.

Figure 20:
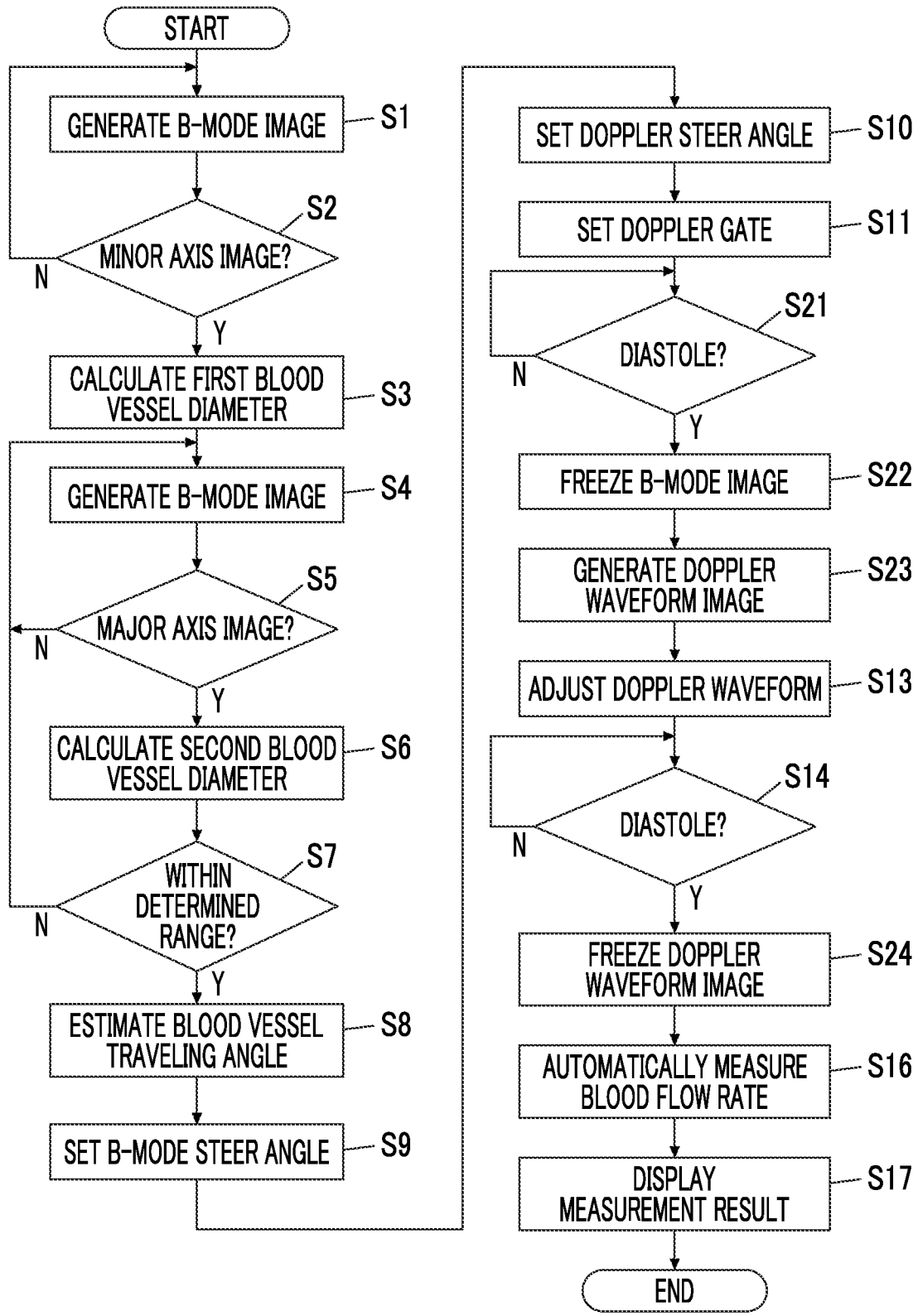
FIG. 20 is a flowchart illustrating an operation of an ultrasound diagnostic apparatus according to a second embodiment of the present invention.

Hereinafter, an operation of the ultrasound diagnostic apparatus 1 according to the second embodiment will be described using the flowchart in FIG. 20. The flowchart is obtained by adding Step S21 to Step S23 instead of Step S12 and adding Step S24 instead of Step S15 to the flowchart of the first embodiment illustrated in FIG. 14.

Thus, the processing of Step S1 to Step S1*l* will not be described.

Figure 21:
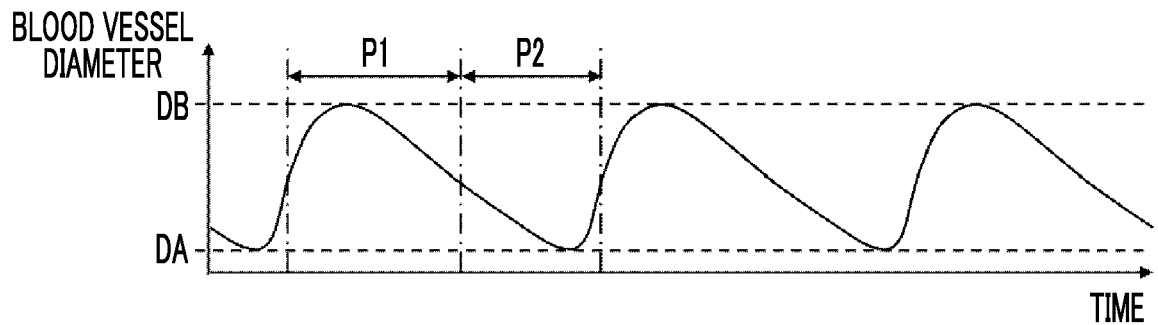
FIG. 21 is a block diagram schematically illustrating a time change of a blood vessel diameter in the second embodiment of the present invention.

In Step S21 subsequent to Step S11, the continuous generation of the B-mode image UB is started, and whether or not the current time point is in the diastole P2 of the heart of the subject is determined based on the value of the second blood vessel diameter DS determined as being within the determined range in Step S7. Here, as illustrated in FIG. 21, in general, the blood vessel diameter periodically changes between the minimum diameter DA and the maximum diameter DB in accordance with the heartbeat, and has the maximum diameter DB in the systole P1 of the heart and has the minimum diameter DA in the diastole P2 of the heart. Thus, for example, in a case where the minimum diameter DA of the blood vessel is measured, it is determined that the current time point is in the diastole P2 of the heart of the subject. In a case where it is determined that the current time point is not in the diastole P2 of the heart of the subject, the processing of Step S21 is performed again. In a case where it is determined that the current time point is in the diastole P2 of the heart of the subject, a transition is made to Step S22.

In Step S22, the display of the B-mode image UB displayed on the display device 9 is frozen.

In subsequent step S23, the Doppler processing unit 7 starts continuously generating the Doppler waveform image UD and displays the generated Doppler waveform image UD on the display device 9. Accordingly, the Doppler waveform image UD is displayed on the display device 9 in a state where the display of the B-mode image UB is frozen on the display device 9.

In this manner, in a case where the Doppler waveform image UD is displayed on the display device 9, a transition is made to Step S13, and the Doppler waveform WD in the Doppler waveform image UD generated in Step S23 is adjusted.

Next, in Step S14, the cycle information of the Doppler waveform WD is acquired, and whether or not the current time point is in the diastole P2 of the heart of the subject is determined based on the acquired cycle information. In a case where it is determined that the current time point is not in the diastole P2 of the heart of the subject, the processing of Step S14 is performed again. In a case where it is determined that the current time point is in the diastole P2 of the heart of the subject, a transition is made to Step S24.

In Step S24, the display of the Doppler waveform image UD displayed on the display device 9 is frozen. Accordingly, the display of the B-mode image UB and the Doppler waveform image UD in the diastole P2 is frozen on the display device 9, and the Doppler data in the diastole P2 in which the amount of change of the Doppler waveform WD is small can be used for measuring the blood flow rate.

In subsequent Step S16, the blood flow rate in the blood vessel region BR is automatically measured based on the value of the second blood vessel diameter DS determined as being within the determined range in Step S7 and the Doppler waveform image UD of which the display is frozen in Step S24. In Step S17, as illustrated in FIG. 17, the measurement value MV of the blood flow rate is displayed on the display device 9 together with the B-mode image UB and the Doppler waveform image UD.

In this manner, in a case where the measurement value MV of the blood flow rate is displayed on the display device 9, the operation of the ultrasound diagnostic apparatus 1 is ended.

As described above, according to the ultrasound diagnostic apparatus 1 according to the second embodiment of the present invention, even in a case where only the Doppler waveform image UD is generated by temporarily stopping the generation of the B-mode image UB, the same applies as in a case of generating both of the B-mode image UB and the Doppler waveform image UD at the same time in the first embodiment. The first blood vessel diameter DF is calculated based on the B-mode image UB representing the minor axis image of the blood vessel B. The B-mode image UB representing the major axis image passing through the center of the blood vessel B is accurately acquired based on the first blood vessel diameter DF. The blood flow rate is measured using the acquired B-mode image UB representing the major axis image of the blood vessel B. Thus, fluctuation of the measurement accuracy of the blood flow rate caused by adjusting the position of the ultrasound probe 21 on the body surface of the subject by the user can be reduced, and the measurement accuracy can be improved.

In Step S21, while a transition is made to next Step S22 based on a trigger that the current time point is in the diastole P2 of the heart of the subject, the trigger for a transition from Step S21 to Step S22 is not limited thereto.

For example, whether or not the current time point is in the systole P1 may be determined instead of determining whether or not the current time point is in the diastole P2. In this case, in a case where it is determined that the current time point is not in the systole P1, whether or not the current time point is in the systole P1 is determined again. In a case where it is determined that the current time point is in the systole P1, a transition is made to subsequent Step S22. However, since the amount of change of the Doppler waveform WD is smaller in the diastole P2 than in the systole P1, it is more preferable to transition to Step S22 based on a trigger that the current time point is in the diastole P2 than to transition to Step S22 based on a trigger that the current time point is in the systole P1.

In addition, for example, Step S21 can be omitted. In this case, the display of the B-mode image UB is frozen on the display device 9 in Step S22 based on a trigger that the Doppler gate DG is set on the B-mode image UB in Step S11.

In addition, for example, a transition can be made to Step S22 based on a trigger that a constant time such as two seconds has elapsed from a time point at which the setting of the Doppler gate DG in Step S11 is completed.

In addition, while the Doppler waveform image UD is generated in Step S23, and the generated Doppler waveform image UD is displayed on the display device 9, the same applies as in Step S12 in the first embodiment. The Doppler waveform image UD may not necessarily be displayed on the display device 9 as long as the data of the Doppler waveform WD is acquired.

Third Embodiment

While the ultrasound diagnostic apparatus 1 of the first embodiment has the configuration in which the display device 9, the input device 18, and the ultrasound probe 21 are directly connected to the processor 22, for example, the display device 9, the input device 18, the ultrasound probe 21, and the processor 22 can be indirectly connected via a network.

Figure 22:
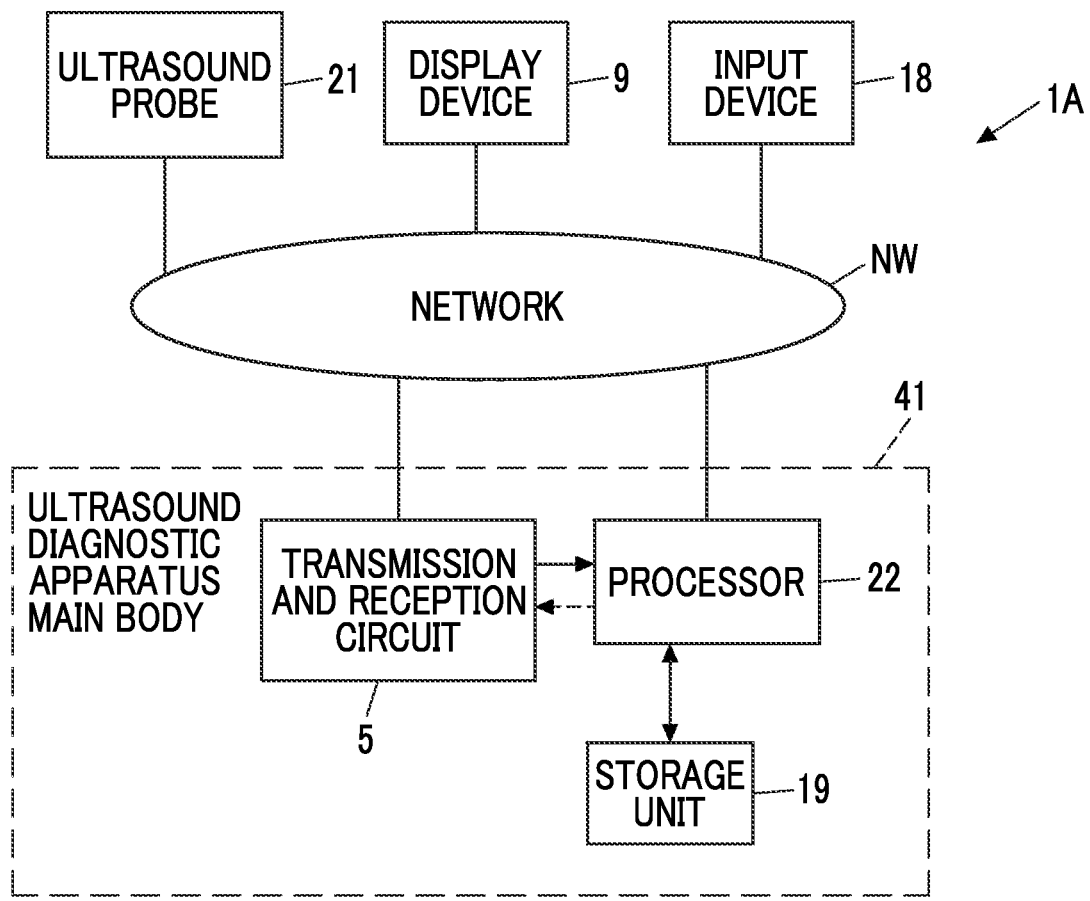
FIG. 22 is a block diagram illustrating a configuration of an ultrasound diagnostic apparatus according to a third embodiment of the present invention.

As illustrated in FIG. 22, in an ultrasound diagnostic apparatus 1A in a third embodiment, the display device 9, the input device 18, and the ultrasound probe 21 are connected to an ultrasound diagnostic apparatus main body 41 via a network NW. The ultrasound diagnostic apparatus main body 41 is obtained by removing the display device 9, the input device 18, and the ultrasound probe 21 in the ultrasound diagnostic apparatus 1 of the first embodiment illustrated in FIG. 1, and is configured with the transmission and reception circuit 5, the storage unit 19, and the processor 22.

Even in a case where the ultrasound diagnostic apparatus 1A has such a configuration, the same applies as in the ultrasound diagnostic apparatus 1 of the first embodiment. The first blood vessel diameter DF is calculated based on the B-mode image UB representing the minor axis image of the blood vessel B. The B-mode image UB representing the major axis image passing through the center of the blood vessel B is accurately acquired based on the first blood vessel diameter DF. The blood flow rate is measured using the acquired B-mode image UB representing the major axis image of the blood vessel B. Thus, fluctuation of the measurement accuracy of the blood flow rate caused by adjusting the position of the ultrasound probe 21 on the body surface of the subject by the user can be reduced, and the measurement accuracy can be improved.

In addition, since the display device 9, the input device 18, and the ultrasound probe 21 are connected to the ultrasound diagnostic apparatus main body 41 via the network NW, the ultrasound diagnostic apparatus main body 41 can be used as a so-called remote server. Accordingly, for example, since the user can perform a diagnosis of the subject by preparing the display device 9, the input device 18, and the ultrasound probe 21 at the hands of the user, convenience in the ultrasound diagnosis can be improved.

In addition, for example, in a case where a portable thin computer referred to as a so-called tablet is used as the display device 9 and the input device 18, the user can more easily perform the ultrasound diagnosis of the subject, and the convenience of the ultrasound diagnosis can be further improved.

While the display device 9, the input device 18, and the ultrasound probe 21 are connected to the ultrasound diagnostic apparatus main body 41 via the network NW, the display device 9, the input device 18, and the ultrasound probe 21 may be connected to the network NW in a wired manner or in a wireless manner.

In addition, while application of an aspect of the third embodiment to the first embodiment is described, the aspect of the third embodiment can also be applied to the second embodiment.

EXPLANATION OF REFERENCES 1, 1A: ultrasound diagnostic apparatus
2: transducer array
3: transmission circuit
4: reception circuit
5: transmission and reception circuit
6: B-mode processing unit
7: Doppler processing unit
8: display control unit
9: display device
10: first vascular wall detection unit
11: first blood vessel diameter calculation unit
12: second vascular wall detection unit
13: second blood vessel diameter calculation unit
14: gate setting unit
15: blood flow velocity calculation unit
16: blood flow rate measurement unit
17: device control unit
18: input device
19: storage unit
21: ultrasound probe
22: processor
23: amplification unit
24: AD conversion unit
25: beam former
26: signal processing unit
27: DSC
28: image processing unit
29: quadrature detection unit
30: high-pass filter
31: fast Fourier transformer
32: Doppler waveform image generation unit
33: data memory
41: ultrasound diagnostic apparatus main body
A1, B1, B2, H: angle
AL, JL: straight line
B: blood vessel
BA: blood vessel traveling angle
BR: blood vessel region
BL: blood vessel gradient line
C: midpoint
E: estimation error
D1: depth direction
D2: lateral direction DA minimum diameter
DB: maximum diameter
DF: first blood vessel diameter
DG: Doppler gate
DS: second blood vessel diameter
G1, G2, G3, G4: graph
J1, J2, J3, J4: depth
K1, K2: brightness threshold value
L1, L2: difference
L1M: maximum value
LG: gate width
M1, M2, M3, M4: measurement point marker
MV: measurement value
NW: network
P1: systole
P2: diastole
R1, R2: search region
SL1, SL2: search line
UB: B-mode image
UD: Doppler waveform image
W1: anterior vascular wall
W2: posterior vascular wall
WD: Doppler waveform
X1, X1M, X2, X2M, X3, X4: point

What is claimed is:

1. An ultrasound diagnostic apparatus comprising:
a display device;
an ultrasound transducer array configured to acquire a reception signal by transmitting and receiving an ultrasound wave to and from a subject; and
a processor configured to
generate a first B-mode image including a minor axis image of a blood vessel based on a first reception signal acquired by the ultrasound transducer array,
display the first B-mode image on the display device,
detect a first vascular wall in the minor axis image by analyzing the first B-mode image,
calculate a first blood vessel diameter based on the detected first vascular wall,
generate a second B-mode image including a major axis image of the blood vessel based on a second reception signal acquired by the ultrasound transducer array,
display the second B-mode image on the display device,
detect a second vascular wall in the major axis image by analyzing the second B-mode image,
calculate a second blood vessel diameter based on the detected second vascular wall, and
once the second blood vessel diameter which is within a determined range with respect to the first blood vessel diameter is calculated,
set a Doppler gate in the blood vessel on the second B-mode image,
acquire Doppler data being complex data in the Doppler gate by performing quadrature detection on the second reception signal corresponding to an image region within the Doppler gate,
calculate a blood flow velocity based on the Doppler data, and
measure a blood flow rate based on any one of the detected second vascular wall or the detected first vascular wall calculated blood flow velocity.

2. The ultrasound diagnostic apparatus according to claim 1,
wherein the processor is further configured to
set a search line for searching for the second vascular wall on the second B-mode image, and
detect an anterior vascular wall and a posterior vascular wall as the second vascular wall based on a brightness profile of the second B-mode image on the search line.

3. The ultrasound diagnostic apparatus according to claim 2,
wherein the processor is further configured to display a detection point marker on the display device by setting the detection point marker on each of the anterior vascular wall and the detected posterior vascular wall.

4. The ultrasound diagnostic apparatus according to claim 2,
wherein the processor is further configured to set the Doppler gate having a center position and a size decided based on coordinates of the anterior vascular wall and the posterior vascular wall.

5. The ultrasound diagnostic apparatus according to claim 3,
wherein the processor is further configured to set the Doppler gate having a center position and a size decided based on coordinates of the anterior vascular wall and the posterior vascular wall.

6. The ultrasound diagnostic apparatus according to claim 2,
wherein the processor is further configured to
estimate a blood vessel traveling angle based on at least one of the anterior vascular wall or the posterior vascular wall and
set a Doppler steer angle such that an angle correction value for the blood vessel traveling angle is within 60 degrees.

7. The ultrasound diagnostic apparatus according to claim 3,
wherein the processor is further configured to
estimate a blood vessel traveling angle based on at least one of the anterior vascular wall or the posterior vascular wall and
set a Doppler steer angle such that an angle correction value for the blood vessel traveling angle is within 60 degrees.

8. The ultrasound diagnostic apparatus according to claim 4,
wherein the processor is further configured to
estimate a blood vessel traveling angle based on at least one of the anterior vascular wall or the posterior vascular wall and
set a Doppler steer angle such that an angle correction value for the blood vessel traveling angle is within 60 degrees.

9. The ultrasound diagnostic apparatus according to claim 6,
wherein the processor is further configured to generate the second B-mode image based on a B-mode steer angle set in accordance with the blood vessel traveling angle.

10. The ultrasound diagnostic apparatus according to claim 7,
wherein the processor is further configured to generate the second B-mode image based on a B-mode steer angle set in accordance with the blood vessel traveling angle.

11. The ultrasound diagnostic apparatus according to claim 8,
wherein the processor is further configured to generate the second B-mode image based on a B-mode steer angle set in accordance with the blood vessel traveling angle.

12. The ultrasound diagnostic apparatus according to claim 1,
wherein the processor is further configured to generate a Doppler waveform image based on the Doppler data, and display both of the second B-mode image and the Doppler waveform image.

13. The ultrasound diagnostic apparatus according to claim 2, wherein the processor is further configured to generate a Doppler waveform image based on the Doppler data, and display both of the second B-mode image and the Doppler waveform image.

14. The ultrasound diagnostic apparatus according to claim 3, wherein the processor is further configured to generate a Doppler waveform image based on the Doppler data, and display both of the second B-mode image and the Doppler waveform image.

15. The ultrasound diagnostic apparatus according to claim 4, wherein the processor is further configured to generate a Doppler waveform image based on the Doppler data, and display both of the second B-mode image and the Doppler waveform image.

16. The ultrasound diagnostic apparatus according to claim 12, wherein the processor is further configured to generate the Doppler waveform image in parallel with the generation of the second B-mode image and measure the blood flow rate by freezing both of the second B-mode image and the Doppler waveform image.

17. The ultrasound diagnostic apparatus according to claim 12, wherein the processor is configured to generate the Doppler waveform image by acquiring the Doppler data in the Doppler gate after the second B-mode image is frozen, and measure the blood flow rate by freezing the Doppler waveform image.

18. The ultrasound diagnostic apparatus according to claim 1, wherein the processor is further configured to, once the calculated second blood vessel diameter maintains the determined range with respect to the calculated first blood vessel diameter over a determined number of frames, automatically measure the blood flow rate.

19. A control method of an ultrasound diagnostic apparatus, the control method comprising:

generating a first B-mode image including a minor axis image of a blood vessel based on a first reception signal acquired by transmitting and receiving an ultrasound wave to and from a subject using an ultrasound transducer array;

displaying the first B-mode image;

detecting a first vascular wall in the minor axis image by analyzing the first B-mode image;

calculating a first blood vessel diameter based on the detected first vascular wall;

generating a second B-mode image including a major axis image of the blood vessel based on a second reception signal acquired by transmitting and receiving an ultrasound wave to and from the subject using the ultrasound transducer array;

displaying the second B-mode image;

detecting a second vascular wall in the major axis image by analyzing the second B-mode image;

calculating a second blood vessel diameter based on the detected second vascular wall; and once the second blood vessel diameter which is within a determined range with respect to the first blood vessel diameter is calculated, setting a Doppler gate in the blood vessel on the second B-mode image;

acquiring Doppler data being complex data in the Doppler gate by performing quadrature detection on the second reception signal corresponding to an image region within the Doppler gate;

calculating a blood flow velocity based on the Doppler data; and measuring a blood flow rate based on any one of the detected second vascular wall or the detected first vascular wall and the calculated blood flow velocity.

20. A processor for an ultrasound diagnostic apparatus, the processor being configured to:

generate a first B-mode image including a minor axis image of a blood vessel based on a first reception signal acquired by transmitting and receiving an ultrasound wave to and from a subject using an ultrasound transducer array;

display the first B-mode image;

detect a first vascular wall in the minor axis image by analyzing the first B-mode image;

calculate a first blood vessel diameter based on the detected first vascular wall;

generate a second B-mode image including a major axis image of the blood vessel based on a second reception signal acquired by transmitting and receiving an ultrasound wave to and from the subject using the ultrasound transducer array;

display the second B-mode image;

detect a second vascular wall in the major axis image by analyzing the second B-mode image;

calculate a second blood vessel diameter based on the detected second vascular wall; and once the second blood vessel diameter which is within a determined range with respect to the first blood vessel diameter is calculated, set a Doppler gate in the blood vessel on the second B-mode image;

acquire Doppler data being complex data in the Doppler gate by performing quadrature detection on the second reception signal corresponding to an image region within the Doppler gate;

calculate a blood flow velocity based on the Doppler data; and measure a blood flow rate based on any one of the detected second vascular wall or the detected first vascular wall and the calculated blood flow velocity.

* * * * *